(12) United States Patent     (10) Patent No.:   US 12,616,517 B2

Okarski et al.     (45) Date of Patent:     May 5, 2026

(54) EXPANDABLE BASKET ASSEMBLIES WITH LINEAR SPINE PATTERNS FOR IMPROVED TISSUE CONTACT AND METHODS FOR MAKING THEREOF

(71) Applicant: Biosense Webster (Israel) Ltd., Yokneam (IL)

(72) Inventors: Kevin Mark Okarski, Monrovia, CA (US); Keshava Datta, Chino Hills, CA (US); Abubakarr Bah, Irvine, CA (US); Thanh Nguyen, El Monte, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 392 days.

(21) Appl. No.: 18/174,409

(22) Filed: Feb. 24, 2023

(65) Prior Publication Data

US 2023/0301713 A1    Sep. 28, 2023

Related U.S. Application Data

(60) Provisional application No. 63/323,849, filed on Mar. 25, 2022.

(51) Int. Cl.
A61B 18/14      (2006.01)
A61B 18/00      (2006.01)

(52) U.S. Cl.
CPC .............................. A61B 18/1492 (2013.01); A61B 2018/00214 (2013.01); A61B 2018/00267 (2013.01);
(Continued)

(58) Field of Classification Search
CPC ...... A61B 18/1492; A61B 2018/00214; A61B 2018/00267; A61B 2018/00273;
(Continued)

(56) References Cited

U.S. PATENT DOCUMENTS 4,699,147 A    10/1987   Chilson et al.
4,940,064 A     7/1990   Desai
(Continued)

FOREIGN PATENT DOCUMENTS

CN     111248993 A    6/2020
CN     111248996 A    6/2020
(Continued)

OTHER PUBLICATIONS

Extended European Search Report and Opinion dated Aug. 4, 2023, from corresponding European Application No. 23164192.9.

*Primary Examiner* — Ronald Hupczey, Jr.
*Assistant Examiner* — Ana Veruska Guerrero

(57) ABSTRACT

The disclosed technology includes an expandable basket assembly for a medical probe, which may include a single unitary structure including a plurality of spines converging at a central spine intersection. The central spine intersection being positioned on a longitudinal axis of the expandable basket assembly at a distal end thereof. The single unitary structure may include a plurality of radial cutouts with each radial cutout defining an opening in each of the plurality of spines proximate the central spine intersection so that each opening extends for a length along each spine away from the central spine intersection.

19 Claims, 30 Drawing Sheets

FIG. 6D

(52) U.S. Cl.
CPC .............. *A61B 2018/00273* (2013.01); *A61B 2018/00279* (2013.01); *A61B 2018/00351* (2013.01); *A61B 2018/00613* (2013.01)

(58) Field of Classification Search
CPC ........... A61B 2018/00279; A61B 2018/00351; A61B 2018/00613; A61B 2018/00029; A61B 2018/0016; A61B 2018/00166; A61B 2018/0022; A61B 2018/00357; A61B 2018/00375; A61B 2018/00577; A61B 2018/00744; A61B 2018/00839; A61B 2018/124; A61B 2018/167; A61B 2034/2051; A61B 2090/065; A61B 2218/002

See application file for complete search history.

(56) References Cited

U.S. PATENT DOCUMENTS

| | | | |
|---|---|---|---|
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,681,280 A | 10/1997 | Rusk et al. | |
| 5,722,401 A | 3/1998 | Pietroski et al. | |
| 5,722,403 A | 3/1998 | McGee et al. | |
| 5,725,525 A | 3/1998 | Kordis | |
| 5,730,128 A | 3/1998 | Pomeranz et al. | |
| 5,772,590 A | 6/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,968,040 A | 10/1999 | Swanson et al. | |
| 6,014,579 A | 1/2000 | Pomeranz et al. | |
| 6,014,590 A | 1/2000 | Whayne et al. | |
| 6,119,030 A | 9/2000 | Morency | |
| 6,216,043 B1 | 4/2001 | Swanson et al. | |
| 6,216,044 B1 | 4/2001 | Kordis | |
| 6,428,537 B1 | 8/2002 | Swanson et al. | |
| 6,456,864 B1 | 9/2002 | Swanson et al. | |
| 6,574,492 B1 | 6/2003 | Ben-Haim et al. | |
| 6,584,345 B2 | 6/2003 | Govari | |
| 6,600,948 B2 | 7/2003 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,522,950 B2 | 4/2009 | Fuimaono et al. | |
| RE41,334 E | 5/2010 | Beatty et al. | |
| 7,846,157 B2 | 12/2010 | Kozel | |
| 7,930,018 B2 | 4/2011 | Harlev et al. | |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,224,416 B2 | 7/2012 | De La Rama et al. | |
| 8,235,988 B2 | 8/2012 | Davis et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 | 3/2017 | Marecki et al. | |
| 9,597,036 B2 | 3/2017 | Aeby et al. | |
| 9,687,297 B2 | 6/2017 | Just et al. | |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 | 10/2018 | Jung et al. | |
| 10,130,420 B2 | 11/2018 | Basu et al. | |
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |
| 10,278,590 B2 | 5/2019 | Salvestro et al. | |
| D851,774 S | 6/2019 | Werneth et al. | |
| 10,314,505 B2 | 6/2019 | Williams et al. | |

(56) References Cited

U.S. PATENT DOCUMENTS

| | | | |
|---|---|---|---|
| 10,314,507 B2 | 6/2019 | Govari et al. | |
| 10,314,648 B2 | 6/2019 | Ge et al. | |
| 10,314,649 B2 | 6/2019 | Bakos et al. | |
| 10,349,855 B2 | 7/2019 | Zeidan et al. | |
| 10,350,003 B2 | 7/2019 | Weinkam et al. | |
| 10,362,991 B2 | 7/2019 | Tran et al. | |
| 10,375,827 B2 | 8/2019 | Weinkam et al. | |
| 10,376,170 B2 | 8/2019 | Quinn et al. | |
| 10,376,221 B2 | 8/2019 | Iyun et al. | |
| 10,398,348 B2 | 9/2019 | Osadchy et al. | |
| 10,403,053 B2 | 9/2019 | Katz et al. | |
| 10,441,188 B2 | 10/2019 | Katz et al. | |
| 10,470,682 B2 | 11/2019 | Deno et al. | |
| 10,470,714 B2 | 11/2019 | Altmann et al. | |
| 10,482,198 B2 | 11/2019 | Auerbach et al. | |
| 10,492,857 B2 | 12/2019 | Guggenberger et al. | |
| 10,542,620 B2 | 1/2020 | Weinkam et al. | |
| 10,575,743 B2 | 3/2020 | Basu et al. | |
| 10,575,745 B2 | 3/2020 | Solis | |
| 10,582,871 B2 | 3/2020 | Williams et al. | |
| 10,582,894 B2 | 3/2020 | Ben Zrihem et al. | |
| 10,596,346 B2 | 3/2020 | Aeby et al. | |
| 10,602,947 B2 | 3/2020 | Govari et al. | |
| 10,617,867 B2 | 4/2020 | Viswanathan et al. | |
| 10,660,702 B2 | 5/2020 | Viswanathan et al. | |
| 10,667,753 B2 | 6/2020 | Werneth et al. | |
| 10,674,929 B2 | 6/2020 | Houben et al. | |
| 10,681,805 B2 | 6/2020 | Weinkam et al. | |
| 10,682,181 B2 | 6/2020 | Cohen et al. | |
| 10,687,892 B2 | 6/2020 | Long et al. | |
| 10,702,178 B2 | 7/2020 | Dahlen et al. | |
| 10,716,477 B2 | 7/2020 | Salvestro et al. | |
| 10,758,304 B2 | 9/2020 | Aujla | |
| 10,765,371 B2 | 9/2020 | Hayam et al. | |
| 10,772,566 B2 | 9/2020 | Aujila | |
| 10,799,281 B2 | 10/2020 | Goertzen et al. | |
| 10,842,558 B2 | 11/2020 | Harlev et al. | |
| 10,842,561 B2 | 11/2020 | Viswanathan et al. | |
| 10,863,914 B2 | 12/2020 | Govari et al. | |
| 10,881,376 B2 | 1/2021 | Shemesh et al. | |
| 10,898,139 B2 | 1/2021 | Guta et al. | |
| 10,905,329 B2 | 2/2021 | Bar-Tal et al. | |
| 10,912,484 B2 | 2/2021 | Ziv-Ari et al. | |
| 10,918,306 B2 | 2/2021 | Govari et al. | |
| 10,939,871 B2 | 3/2021 | Altmann et al. | |
| 10,952,795 B2 | 3/2021 | Cohen et al. | |
| 10,973,426 B2 | 4/2021 | Williams et al. | |
| 10,973,461 B2 | 4/2021 | Baram et al. | |
| 10,987,045 B2 | 4/2021 | Basu et al. | |
| 11,006,902 B1 | 5/2021 | Bonyak et al. | |
| 11,040,208 B1 | 6/2021 | Govari et al. | |
| 11,045,628 B2 | 6/2021 | Beeckler et al. | |
| 11,051,877 B2 | 7/2021 | Sliwa et al. | |
| 11,109,788 B2 | 9/2021 | Rottmann et al. | |
| 11,116,435 B2 | 9/2021 | Urman et al. | |
| 11,129,574 B2 | 9/2021 | Cohen et al. | |
| 11,160,482 B2 | 11/2021 | Solis | |
| 11,164,371 B2 | 11/2021 | Yellin et al. | |
| 2002/0198522 A1 | 12/2002 | Kordis | |
| 2004/0210121 A1 | 10/2004 | Fuimaono et al. | |
| 2006/0009689 A1 | 1/2006 | Fuimaono et al. | |
| 2006/0009690 A1 | 1/2006 | Fuimaono et al. | |
| 2006/0100669 A1 | 5/2006 | Fuimaono et al. | |
| 2007/0093806 A1 | 4/2007 | Desai et al. | |
| 2007/0276212 A1 | 11/2007 | Fuimaono et al. | |
| 2008/0234564 A1 | 9/2008 | Beatty et al. | |
| 2011/0118726 A1 | 5/2011 | De La Rama et al. | |
| 2011/0160574 A1 | 6/2011 | Harlev et al. | |
| 2011/0190625 A1 | 8/2011 | Harlev et al. | |
| 2011/0245756 A1 | 10/2011 | Arora et al. | |
| 2011/0301597 A1 | 12/2011 | McDaniel et al. | |
| 2012/0271140 A1* | 10/2012 | Kordis | A61B 5/283 |
| | | | 600/375 |
| 2013/0090651 A1 | 4/2013 | Smith | |
| 2013/0172872 A1 | 7/2013 | Subramaniam et al. | |
| 2013/0172883 A1 | 7/2013 | Lopes et al. | |
| 2013/0178850 A1 | 7/2013 | Lopes et al. | |
| 2013/0190587 A1 | 7/2013 | Lopes et al. | |
| 2013/0296852 A1 | 11/2013 | Madjarov et al. | |
| 2014/0025069 A1 | 1/2014 | Willard et al. | |
| 2014/0052118 A1 | 2/2014 | Laske et al. | |
| 2014/0180147 A1 | 6/2014 | Thakur et al. | |
| 2014/0180151 A1 | 6/2014 | Maskara et al. | |
| 2014/0180152 A1 | 6/2014 | Maskara et al. | |
| 2014/0257069 A1 | 9/2014 | Eliason et al. | |
| 2014/0276712 A1 | 9/2014 | Mallin et al. | |
| 2014/0309512 A1 | 10/2014 | Govari et al. | |
| 2014/0336494 A1 | 11/2014 | Just et al. | |
| 2015/0011991 A1 | 1/2015 | Buysman et al. | |
| 2015/0045863 A1 | 2/2015 | Litscher et al. | |
| 2015/0080693 A1 | 3/2015 | Solis | |
| 2015/0105770 A1 | 4/2015 | Amit | |
| 2015/0119878 A1 | 4/2015 | Heisel et al. | |
| 2015/0133919 A1 | 5/2015 | McDaniel et al. | |
| 2015/0208942 A1 | 7/2015 | Bar-Tal et al. | |
| 2015/0223757 A1 | 8/2015 | Werneth et al. | |
| 2015/0250424 A1 | 9/2015 | Govari et al. | |
| 2015/0270634 A1 | 9/2015 | Buesseler et al. | |
| 2015/0342532 A1 | 12/2015 | Basu et al. | |
| 2016/0081746 A1 | 3/2016 | Solis | |
| 2016/0113582 A1 | 4/2016 | Altmann et al. | |
| 2016/0113709 A1 | 4/2016 | Maor | |
| 2016/0183877 A1 | 6/2016 | Williams et al. | |
| 2016/0228023 A1 | 8/2016 | Govari | |
| 2016/0228062 A1 | 8/2016 | Altmann et al. | |
| 2016/0278853 A1 | 9/2016 | Ogle et al. | |
| 2016/0302858 A1 | 10/2016 | Bencini | |
| 2016/0338770 A1 | 11/2016 | Bar-Tal et al. | |
| 2017/0027638 A1 | 2/2017 | Solis | |
| 2017/0065227 A1 | 3/2017 | Marrs et al. | |
| 2017/0071543 A1 | 3/2017 | Basu et al. | |
| 2017/0071544 A1 | 3/2017 | Basu et al. | |
| 2017/0071665 A1 | 3/2017 | Solis | |
| 2017/0095173 A1 | 4/2017 | Bar-Tal et al. | |
| 2017/0100187 A1 | 4/2017 | Basu et al. | |
| 2017/0143227 A1 | 5/2017 | Marecki et al. | |
| 2017/0156790 A1 | 6/2017 | Aujla | |
| 2017/0172442 A1 | 6/2017 | Govari | |
| 2017/0185702 A1 | 6/2017 | Auerbach et al. | |
| 2017/0202515 A1 | 7/2017 | Zrihem et al. | |
| 2017/0221262 A1 | 8/2017 | Laughner et al. | |
| 2017/0224958 A1 | 8/2017 | Cummings et al. | |
| 2017/0265812 A1 | 9/2017 | Williams et al. | |
| 2017/0281031 A1 | 10/2017 | Houben et al. | |
| 2017/0281268 A1 | 10/2017 | Tran et al. | |
| 2017/0296125 A1 | 10/2017 | Altmann et al. | |
| 2017/0296251 A1 | 10/2017 | Wu et al. | |
| 2017/0319140 A1 | 11/2017 | Wu et al. | |
| 2017/0347959 A1 | 12/2017 | Guta et al. | |
| 2017/0354338 A1 | 12/2017 | Levin et al. | |
| 2017/0354339 A1 | 12/2017 | Zeidan et al. | |
| 2017/0354364 A1 | 12/2017 | Bar-Tal et al. | |
| 2018/0008203 A1 | 1/2018 | Iyun et al. | |
| 2018/0028084 A1 | 2/2018 | Williams et al. | |
| 2018/0049803 A1 | 2/2018 | Solis | |
| 2018/0085064 A1 | 3/2018 | Auerbach et al. | |
| 2018/0132749 A1 | 5/2018 | Govari et al. | |
| 2018/0137687 A1 | 5/2018 | Katz et al. | |
| 2018/0160936 A1 | 6/2018 | Govari et al. | |
| 2018/0160978 A1 | 6/2018 | Cohen et al. | |
| 2018/0168511 A1 | 6/2018 | Hall et al. | |
| 2018/0184982 A1 | 7/2018 | Basu et al. | |
| 2018/0192958 A1 | 7/2018 | Wu | |
| 2018/0206792 A1 | 7/2018 | Auerbach et al. | |
| 2018/0228439 A1* | 8/2018 | Wu | A61B 5/6859 |
| 2018/0235692 A1 | 8/2018 | Efimov et al. | |
| 2018/0249959 A1 | 9/2018 | Osypka | |
| 2018/0256109 A1 | 9/2018 | Wu et al. | |
| 2018/0279954 A1 | 10/2018 | Hayam et al. | |
| 2018/0303414 A1 | 10/2018 | Toth et al. | |
| 2018/0310987 A1 | 11/2018 | Altmann et al. | |
| 2018/0311497 A1 | 11/2018 | Viswanathan et al. | |
| 2018/0338722 A1 | 11/2018 | Altmann et al. | |
| 2018/0344188 A1 | 12/2018 | Govari | |

(56)  References Cited

U.S. PATENT DOCUMENTS

| | | |
|---|---|---|
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Mswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0163707 A1 | 5/2020 | Sliwa et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077180 A1 | 3/2021 | Govari et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161592 A1 | 6/2021 | Altmann et al. |
| 2021/0162210 A1 | 6/2021 | Altmann et al. |
| 2021/0169421 A1 | 6/2021 | Govari |
| 2021/0169550 A1 | 6/2021 | Govari et al. |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0177503 A1 | 6/2021 | Altmann et al. |
| 2021/0178166 A1 | 6/2021 | Govari et al. |
| 2021/0186363 A1 | 6/2021 | Gliner et al. |
| 2021/0186604 A1 | 6/2021 | Altmann et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |
| 2022/0110679 A1* | 4/2022 | Wang ................. A61B 18/1492 |
| 2023/0225787 A1* | 7/2023 | Okarski ............. A61B 18/1492 |
| | | 606/41 |
| 2023/0301712 A1* | 9/2023 | Okarski ............. A61B 18/1492 |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |

(56)              References Cited

FOREIGN PATENT DOCUMENTS

| WO | 2018191149 A1 | 10/2018 | |
|----|---------------|---------|---|
| WO | 2019084442 A1 | 5/2019 | |
| WO | 2019143960 A1 | 7/2019 | |
| WO | 2020026217 A1 | 2/2020 | |
| WO | 2020206328 A1 | 10/2020 | |
| WO | 2020251857 A1 | 12/2020 | |
| WO | WO-2022001908 A1 * | 1/2022 | ......... A61B 18/1492 |

* cited by examiner

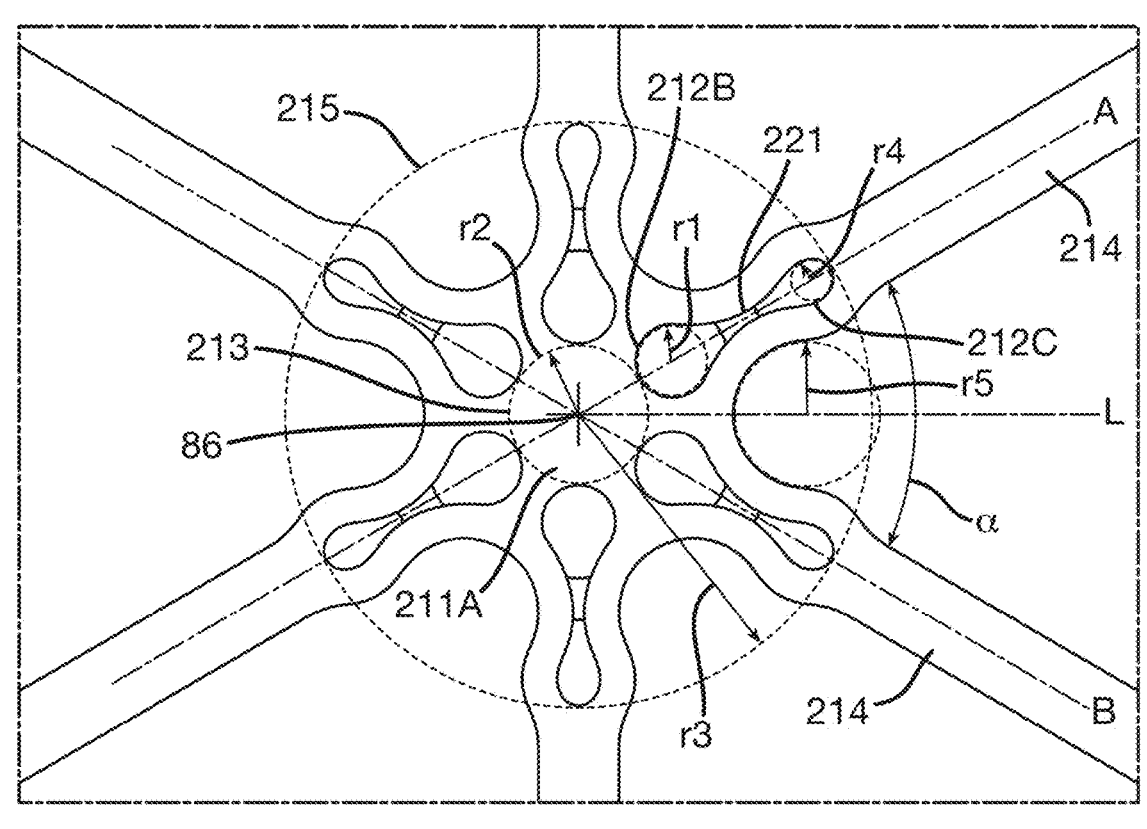
FIG. 6E1
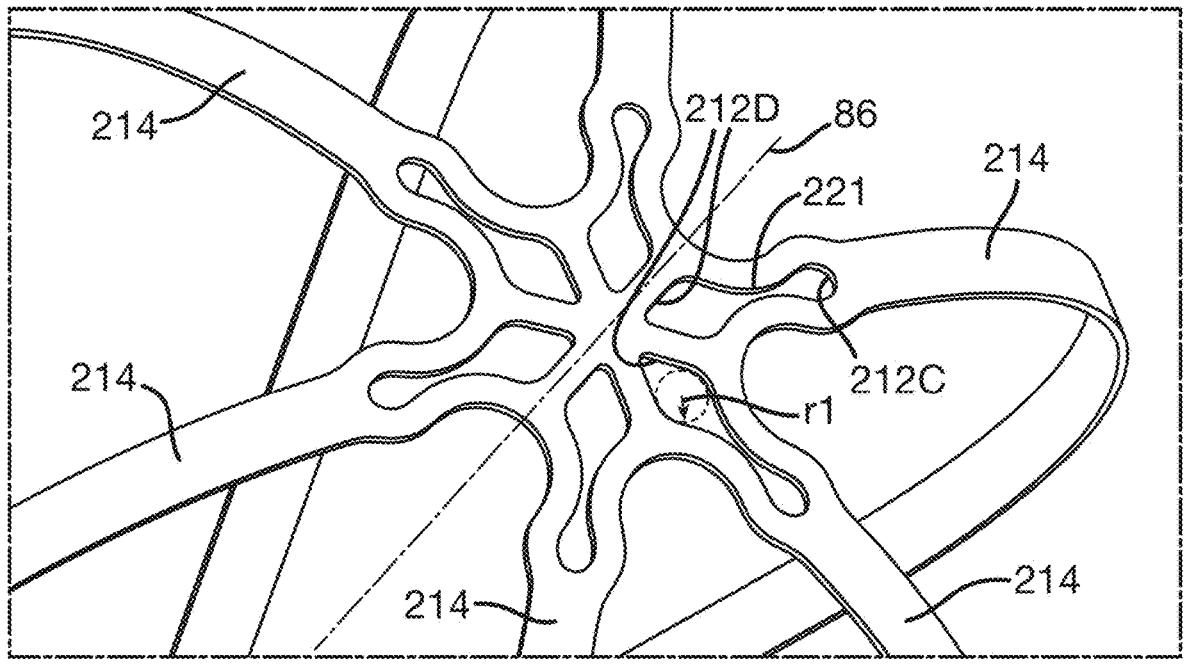
FIG. 6E2

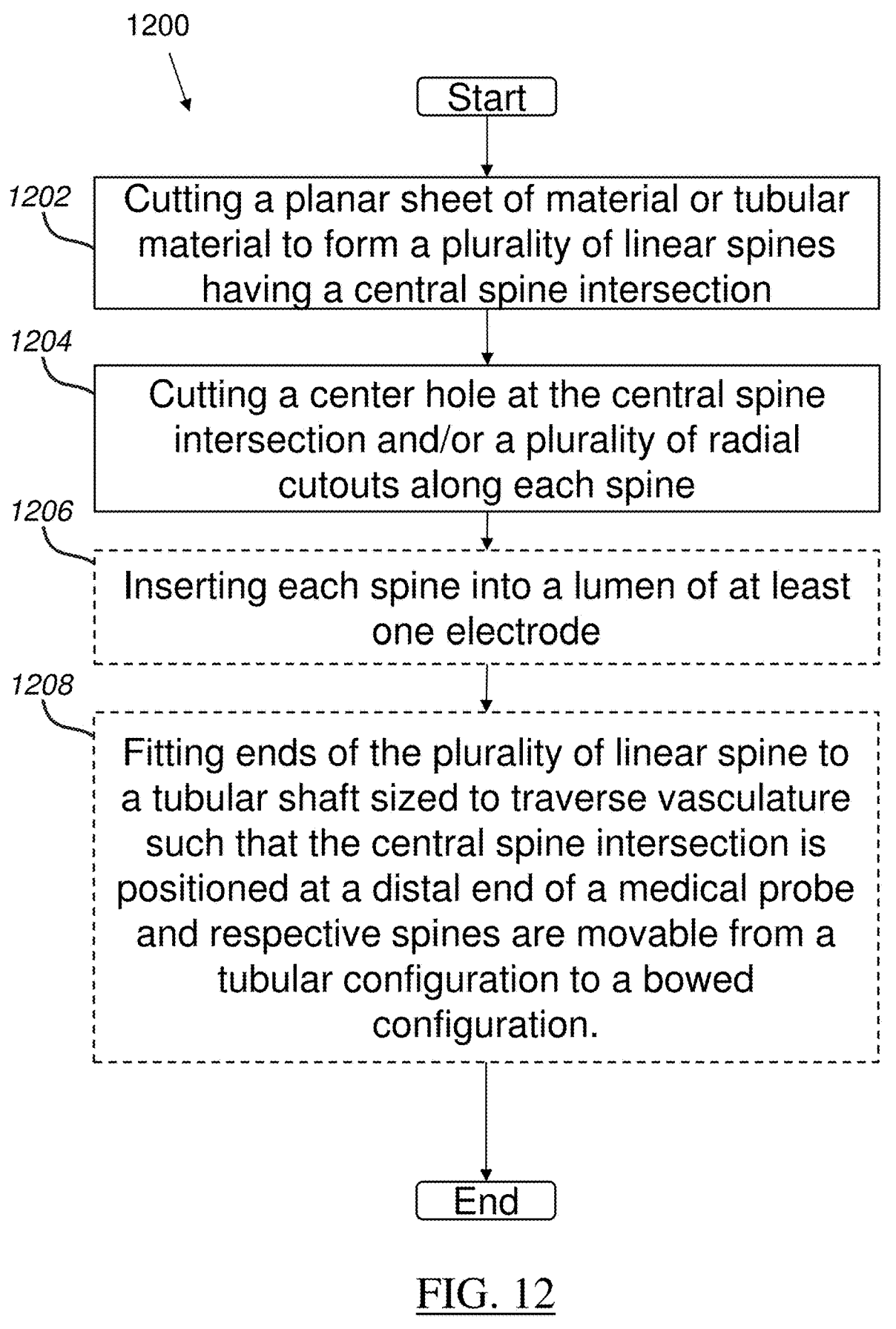

1200

Start

1202

Cutting a planar sheet of material or tubular material to form a plurality of linear spines having a central spine intersection

1204

Cutting a center hole at the central spine intersection and/or a plurality of radial cutouts along each spine

1206

Inserting each spine into a lumen of at least one electrode

1208

Fitting ends of the plurality of linear spine to a tubular shaft sized to traverse vasculature such that the central spine intersection is positioned at a distal end of a medical probe and respective spines are movable from a tubular configuration to a bowed configuration.

End

FIG. 12

EXPANDABLE BASKET ASSEMBLIES WITH LINEAR SPINE PATTERNS FOR IMPROVED TISSUE CONTACT AND METHODS FOR MAKING THEREOF

CROSS-REFERENCE TO RELATED APPLICATION

This application claims priority under 35 U.S.C. § 119 to U.S. Provisional Patent Application No. 63/323,849, filed Mar. 25, 2022, the entire contents of which are incorporated herein by reference.

FIELD

The present invention relates generally to medical devices, and in particular catheters with expandable basket assemblies and electrodes, and further relates to, but not exclusively, catheters suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art tend to utilize radiofrequency (RF) electrical energy to heat tissue. RF ablation can have certain rare drawbacks due to operator's skill, such as heightened risk of thermal cell injury which can lead to tissue charring, burning, steam pop, phrenic nerve palsy, pulmonary vein stenosis, and esophageal fistula. Cryoablation is an alternative approach to RF ablation that generally reduces thermal risks associated with RF ablation but may present tissue damage due to the very low temperature nature of such devices. Maneuvering cryoablation devices and selectively applying cryoablation, however, is generally more challenging compared to RF ablation; therefore cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. Nos. 2021/0169550A1, 2021/0169567A1, 2021/0169568A1, 2021/0161592A1, 2021/0196372A1, 2021/0177503A1, 2021/0186604A1, 2021/0162210, and 2021/0077180, each of which are incorporated herein by reference and attached in the Appendix of parent application 63/323,849.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Furthermore, multiple linear spines are generally assembled together by attaching both ends of the linear spines to a tubular shaft (e.g., a pusher tube) to form a spherical basket. Due to the small size of the spines and the electrodes, however, adhering the electrodes to the spines and then forming a spherical basket from the multiple linear spines can be a difficult task, increasing the manufacturing time and cost and the chances that the electrode fails due to an improper bond or misalignment. What is needed, therefore, are devices and methods of forming an improved basket assembly that can help to reduce the time required for manufacturing the basket assembly and alternative catheter geometries in general.

SUMMARY

Various embodiments of an expandable basket assembly for a medical probe and related methods are described and illustrated. An expandable basket assembly for a medical probe may include a single unitary structure comprising a plurality of spines converging at a central spine intersection. The central spine intersection may be positioned on a longitudinal axis of the expandable basket assembly at a distal end thereof. The single unitary structure may include a plurality of radial cutouts with each radial cutout defining an opening in each of the plurality of spines proximate the central spine intersection so that each opening extends for a length along each spine away from the central spine intersection.

Each cut-out may include a tadpole shaped cutout. The tadpole cutout may include a head portion contiguous to a circumference of a first virtual circle with a first radius $r1$ disposed about the central axis. The head portion may define a negative area approximating a second virtual circle with a second radius $r2$. The head portion may be connected to a slotted tail portion extending for a first length $L1$ along the spine and contiguous to an inside circumference of a third virtual circle having a third radius $r3$.

The first length of the slotted tail portion may be approximately 6-10 times that of the length of the radius $r1$ of the first virtual circle.

A center aperture may be disposed on the central spine intersection and the plurality of radial cutouts may be separated from the center aperture by a portion of the central spine intersection.

A cut-out may be disposed on the central axis to define a central negative area approximating a central circle including a central radius $r0$ smaller than the first radius $r1$.

The negative area of each of the tadpole cut-out may include approximately 0.2 mm-squared while the negative area of center aperture 212A may be approximately 0.05 mm-squared so that the total negative area defined by all of the cut-outs may be approximately 1.4 mm-squared.

A central void radius $r0$ may be approximately 0.13 mm, the second radius $r2$ may be approximately 0.2 mm, and the first radius $r1$ may be approximately 0.23 mm.

The center aperture may include an area of about 0.01 mm-squared to about 0.4 mm-squared.

Each of the plurality of radial cutouts may include an area of about 0.1 mm-squared to about 0.55 mm-squared.

Each of the spines may include a first portion proximate to the central spine intersection with a first width, a second portion proximate the first portion with a second width less than the first portion, and a third portion proximate the second portion with a third width that is greater than the first width and greater than the second width.

Each radial cut-out may define a comet-shaped cutout with head portion with a slotted tapered tail extending to the proximal portion of each spine.

The first width may be about 0.15 mm to about 0.5 mm, the second width may be about 0.05 mm to about 0.35 mm, and the third width may be about 0.3 mm to about 0.7 mm.

The third portion of each spine may include an electrode attachment slot configured to accept an electrode. The electrode attachment slot may bisect each spine into two minor widths of about 0.05 mm to about 6 mm.

Each radial cut-out may include two teardrop cutouts attached at their narrow portions to define a single cutout on each spine of about 0.4 mm-squared.

The plurality of radial cutouts may extend from and are connected to the center aperture to form a single cutout.

The third portion of each spine may include a slot that bisects each spine into two minor widths each of which comprises a width of approximately 0.1 mm to approximately 6 mm.

The third portion of each spine may include a slot that bisects each spine into two minor portions with the slot comprising a width of approximately 0.05 mm to approximately 0.55 mm.

The center aperture may include a radius of approximately 0.4 mm to approximately 1.2 mm.

Each radial cutout may include an ellipse shape at an end furthest from the center aperture.

The ellipse shape may include a length of about 0.20 mm to about 0.55 mm and a width of about 0.1 mm to about 0.45 mm.

Each radial cutout may include a circular shape at an end furthest from the center aperture.

The circular shape may include a radius of approximately 0.05 mm to approximately 0.6 mm.

Each spine may include a thickness of about 0.03 mm to about 0.15 mm.

Each spine may include two connecting portions that connect to adjacent spines.

The connecting portions may include a width of about 0.12 mm to about 0.4 mm.

Two adjacent connecting portions may form a circular shape.

The circular shape may include a radius of approximately 0.25 mm to approximately 0.75 mm.

The plurality of spines may extend from the central spine intersection in an equiangular pattern such that respective angles between respectively adjacent spines are approximately equal.

The plurality of spines may include four to ten spines of the plurality of spines.

The plurality of spines may include six spines.

The plurality of spines may form an approximately spherical shape.

The plurality of spines may form an approximately oblate-spheroid shape.

The plurality of radial cutouts may include a centrosymmetric pattern.

The plurality of spines may include nitinol.

The plurality of spines may include cobalt chromium.

One or more electrodes may be coupled to each of the spines. Each electrode may define a lumen through the electrode so that a spine extends through the lumen of each of the one or more electrodes.

Each electrode may include a wire relief adjacent the lumen to allow for one or more wires to extend adjacent to the lumen.

The lumen may be disposed symmetrically about a longitudinal axis of the electrode.

The one or more electrodes may be configured to deliver electrical pulses for irreversible electroporation, the pulses having a peak voltage of at least 900 volts (V).

In an aspect, an expandable basket assembly for a medical probe may include a single unitary structure that may include a plurality of spines converging at a central spine intersection in a spiral pattern. The central spine intersection may be positioned on a longitudinal axis of the expandable basket assembly at a distal end thereof. Each of the plurality of spines may include a first width extending away from the distal end and a second width associated with the spiral pattern and narrower than the first width.

The spiral pattern may be logarithmic.

Each spine may include a pitch angle of approximately 60 degrees to approximately 105 degrees.

Each spine may include a pitch angle of approximately 100 degrees to approximately 140 degrees.

The central spine intersection may include a center aperture.

The center aperture may include a radius of approximately 0.01 mm to approximately 0.3 mm.

The first width may be approximately 0.1 mm to approximately 1.0 mm.

The second width may be approximately 0.05 mm to approximately 0.65 mm.

Each spine may include a tapering width disposed between the first and second widths.

One or more electrodes may be coupled to each of the spines. Each electrode may define a lumen through the electrode so that a spine extends through the lumen of each of the one or more electrodes.

Each electrode may include a wire relief adjacent the lumen to allow for one or more wires to extend adjacent to the lumen.

The lumen may be disposed symmetrically about a longitudinal axis of the electrode.

The one or more electrodes may be configured to deliver electrical pulses for irreversible electroporation, the pulses having a peak voltage of at least 900 volts (V).

In an aspect, an expandable basket assembly for a medical probe may include a single unitary structure that may include a plurality of spines converging at a central spine intersection. The central spine intersection may be positioned on a longitudinal axis of the expandable basket assembly at a distal end thereof. Each of the plurality of spines may include a first portion proximate the distal end, a second portion proximate the first portion, and a third portion proximate the second portion and wider than the first portion. The central spine intersection may include a center aperture.

The first portion may include a first width of approximately 0.05 mm to approximately 0.65 mm.

The third portion may include a third width of approximately 0.1 mm to approximately 1.0 mm.

The second portion may include a tapering width narrowing from the first portion to the third portion.

One or more electrodes may be coupled to each of the spines. Each electrode may define a lumen through the electrode so that a spine extends through the lumen of each of the one or more electrodes.

Each electrode may include a wire relief adjacent the lumen to allow for one or more wires to extend adjacent to the lumen.

The lumen is disposed symmetrically about a longitudinal axis of the electrode.

The one or more electrodes may be configured to deliver electrical pulses for irreversible electroporation, the pulses having a peak voltage of at least 900 volts (V).

In an aspect, a method of constructing a medical probe may include cutting a planar sheet or tubular stock of material to form a plurality of spines having a central spine intersection and cutting a center aperture at the central spine intersection, cutting a plurality of radial cutouts with each radial cutout positioned on each spine of the plurality of spines, or cutting both the center aperture and the plurality of radial cutouts.

The center aperture may be cut to have an area of approximately 0.01 mm-squared to approximately 0.4 mm-squared.

The method also including cutting a plurality of radial cutouts with each radial cutout positioned on each spine of the plurality of spines.

Each of the plurality of radial cutouts may be cut to have an area of approximately 0.1 mm-squared to approximately 0.55 mm-squared.

Each of the spines may include a first portion distal to the central spine intersection with a first width, a second portion proximate the first portion with a second width less than the first width, and a third portion proximate the second portion and the central spine intersection with a third width that is less than the first width and greater than the second width.

The first width may be approximately 0.3 mm to approximately 0.7 mm, the second width may be approximately 0.05 to approximately 0.35 mm, and the second width may be approximately 0.15 mm to approximately 0.5 mm.

The plurality of radial cutouts may extend from and are connected to the center aperture to form a single cutout.

Cutting the plurality of radial cutouts and cutting the center aperture may occur simultaneously.

The center aperture may include a radius of approximately 0.4 mm to approximately 1.2 mm.

Each radial cutout may be cut to form an ellipse shape at an end furthest from the center aperture.

The ellipse shape may include a length of approximately 0.20 mm to 0.55 mm and a width of approximately 0.1 mm to 0.45 mm.

Each spine may be cut to a thickness of approximately 0.03 mm to approximately 0.15 mm.

Cutting the plurality of spines may include cutting a connecting portion that connects to adjacent spines about a central spine intersection.

The connecting portion may be cut to a width of approximately 0.12 mm to approximately 0.4 mm.

Two adjacent connecting portions may be cut to form a circular shape.

The circular shape may be cut to have a radius of approximately 0.25 mm to approximately 0.75 mm.

The method may also include inserting each spine into a lumen of one or more electrodes and fitting ends of the plurality of spines to a tubular shaft sized to traverse vasculature such that the central spine intersection is positioned at a distal end of the medical probe and respective spines are movable from a tubular configuration to a bowed configuration.

Each electrode may include a relief adjacent the lumen to allow a wire to extend adjacent to the lumen.

The wire may be electrically insulated from the single spine.

The method may also include electrically connecting the wire to the one or more electrodes.

The plurality of spines may be cut from the tubular stock of material using one or more lasers.

BRIEF DESCRIPTION OF THE DRAWINGS

FIGS. 6A, 6B, 6C, 6D, 6E, 6E1, 6E2, 6F, 6G, 6H, 6I, 6J, and 6K are schematic pictorial illustrations of central spine intersections, in accordance with an embodiment of the present invention;

FIG. 12 is a flowchart illustrating a method of assembling a basket assembly, in accordance with an embodiment of the present invention.

DETAILED DESCRIPTION

Figure 1:
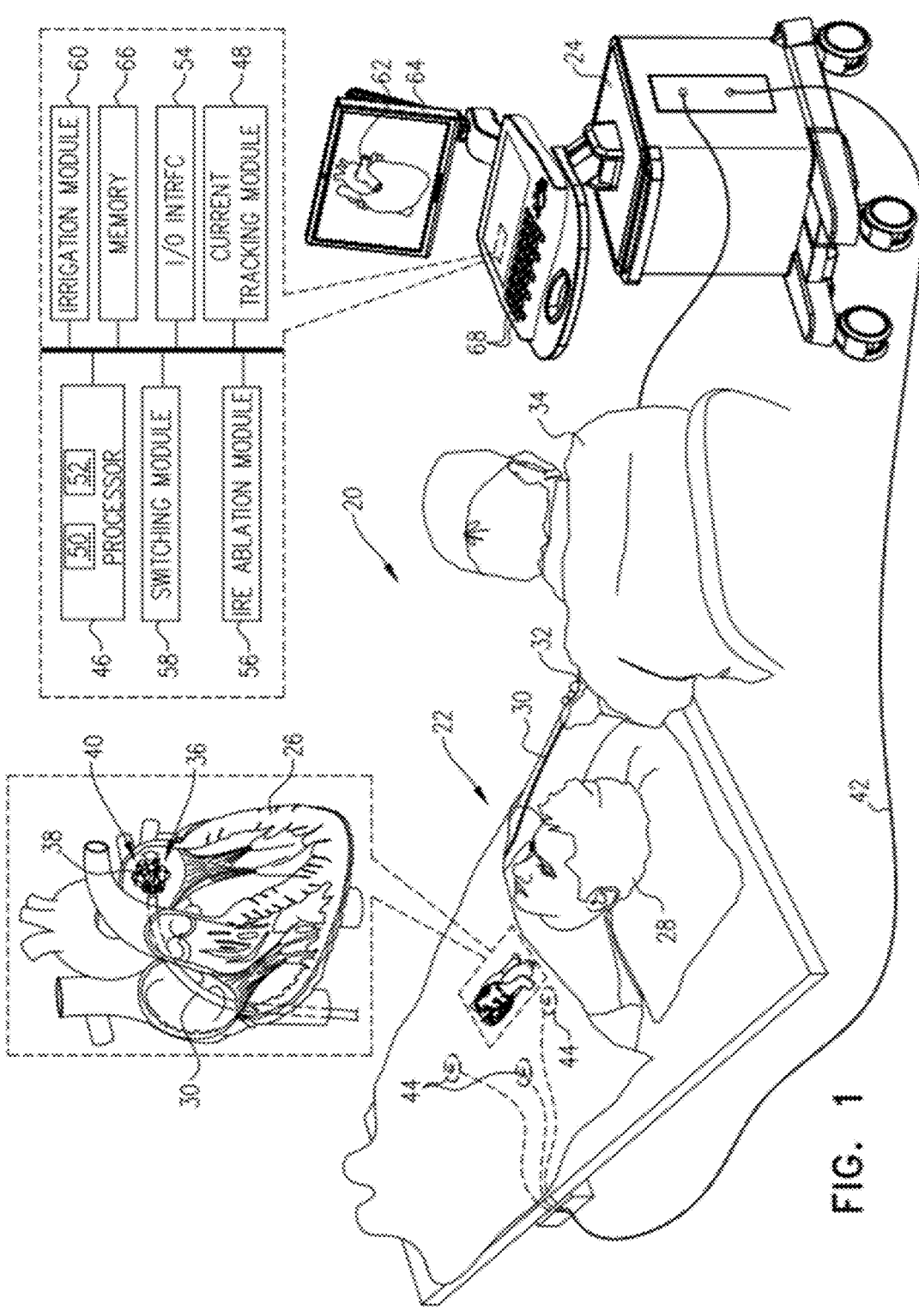
FIG. 1 is a schematic pictorial illustration of a medical system including a medical probe whose distal end includes a basket assembly with electrodes, in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 110%.

As used herein, the terms "patient," "host," "user," and "subject" refer to any human or animal subject and are not intended to limit the systems or methods to human use, although use of the subject invention in a human patient represents a preferred embodiment. In addition, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example. As well, the term "proximal" indicates a location closer to the operator or physician whereas "distal" indicates a location further away to the operator or physician.

As discussed herein, "operator" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode including a high current density and high electric flux density is positioned at a treatment site, and a second electrode including comparatively lower current density and lower electric flux density is positioned remotely from the treatment site.

As discussed herein, the terms "biphasic pulse" and "monophasic pulse" refer to respective electrical signals. "Biphasic pulse" refers to an electrical signal including a positive-voltage phase pulse (referred to herein as "positive phase") and a negative-voltage phase pulse (referred to herein as "negative phase"). "Monophasic pulse" refers to an electrical signal including only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape including an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The term "temperature rating", as used herein, is defined as the maximum continuous temperature that a component can withstand during its lifetime without causing thermal damage, such as melting or thermal degradation (e.g., charring and crumbling) of the component.

The present disclosure is related to systems, methods or uses and devices which utilize end effectors including electrodes affixed to spines. Example systems, methods, and devices of the present disclosure may be particularly suited for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation.

RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore, cryoablation is not viable in certain anatomical geometries which may be reached by electrical ablation devices.

IRE as discussed in this disclosure is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by programmed cell death or apoptosis, which is believed to leave less scar tissue as compared to other ablation modalities. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The solution of this disclosure includes systems and methods for applying electrical signals from catheter electrodes positioned in the vicinity of myocardial tissue, preferably by applying a pulsed electric field effective to induce electroporation in the myocardial tissue. The systems and methods can be effective to ablate targeted tissue by inducing irreversible electroporation. In some examples, the systems and methods can be effective to induce reversible electroporation as part of a diagnostic procedure. Reversible electroporation occurs when the electricity applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated herein by reference and attached in the Appendix of parent application 63/323,849.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0169550A1, 2021/0169567A1, 2021/0169568A1, 2021/0161592A1, 2021/0196372A1, 2021/0177503A1, 2021/0186604A1, 2021/0162210, and 2021/0077180 the entireties of each of which are incorporated herein by reference and attached in the Appendix of parent application 63/323,849.

To deliver pulsed field ablation (PFA) in an IRE (irreversible electroporation) procedure, electrodes should contact the tissue being ablated with a sufficiently large surface area. As described hereinbelow, the medical probe includes a tubular shaft including proximal and distal ends, and a basket assembly at the distal end of the tubular shaft. The basket assembly includes a single unitary structure. The unitary structure can include a plurality of linear spines formed from a planar sheet of material and one or more electrodes coupled to each of the spines. The plurality of linear spines can converge at a central spine intersection including one or more cutouts. The cutouts can allow for bending of each spine such that the spines form an approximately spherical or oblate-spheroid basket assembly. It is noted that the cutouts (in various configurations described and illustrated in the specification) allows the basket to be compressed into a much smaller form factor when undeployed (or undergoing a retraction into a delivery sheath) without buckling or plastic deformation.

FIG. 1 is a schematic, pictorial illustration of a medical system 20 including a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Medical probe 22 includes a flexible insertion tube 30 and a handle 32 coupled to a proximal end of the tubular shaft. During a medical procedure, a medical professional 34 can insert probe 22 through the vascular system of patient 28 so that a distal end 36 of the medical probe enters a body cavity such as a chamber of heart 26. Upon distal end 36 entering the chamber of heart 26, medical professional 34 can deploy a basket assembly 38 approximate a distal end 36 of the medical probe 22. Basket assembly 38 can include a plurality of electrodes 40 affixed to a plurality of spines 214, as described in the description referencing FIGS. 2A and 2B hereinbelow. To start performing a medical procedure such as irreversible electroporation (IRE) ablation, medical professional 34 can manipulate handle 32 to position distal end 36 so that electrodes 40 engage cardiac tissue at a desired location or locations. Upon positioning the distal end 36 so that electrodes 40 engages cardiac tissue, the medical professional 34 can activate the medical probe 22 such that electrical pulses are delivered by the electrodes 40 to perform the IRE ablation.

Figures 2A, 2B:
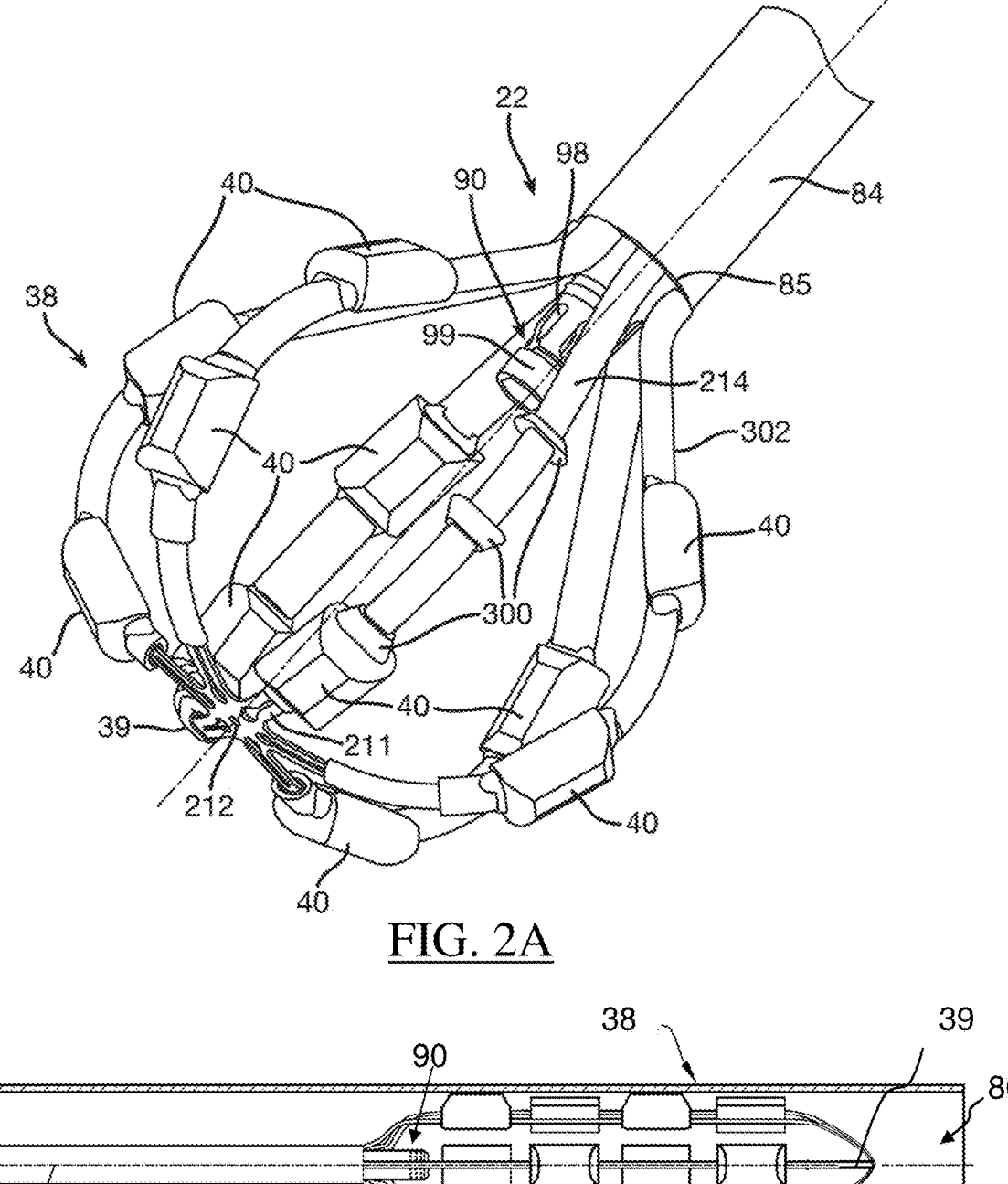
FIG. 2A is a schematic pictorial illustration showing a perspective view of a medical probe in an expanded form, in accordance with an embodiment of the present invention.
FIG. 2B is a schematic pictorial illustration showing a side view of a medical probe in a collapsed form, in accordance with embodiments of the present invention.
Figure 2C:
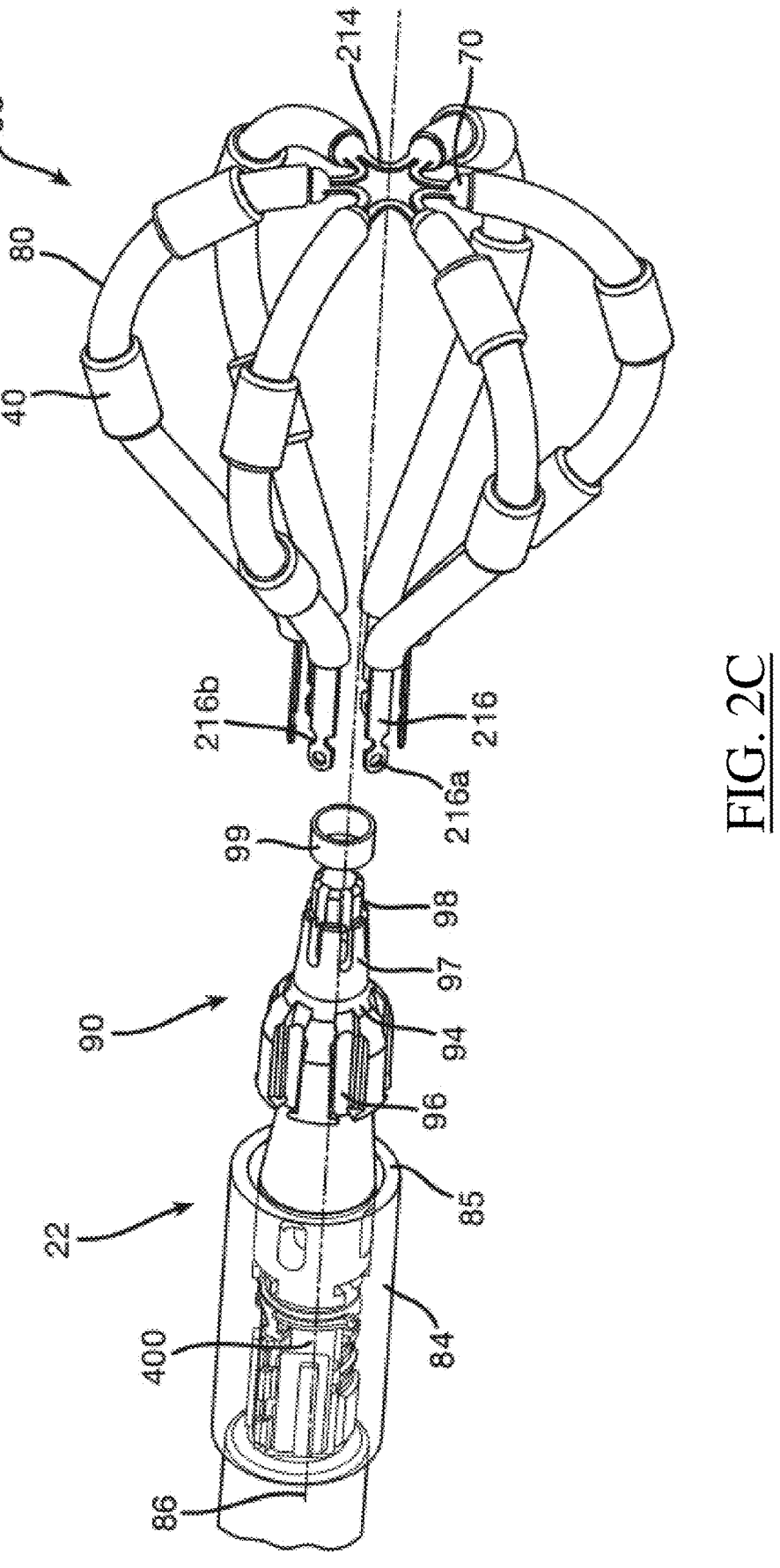
FIG. 2C is a schematic pictorial illustration showing an exploded side view of a medical probe, in accordance with an embodiment of the present invention.
Figure 2D:
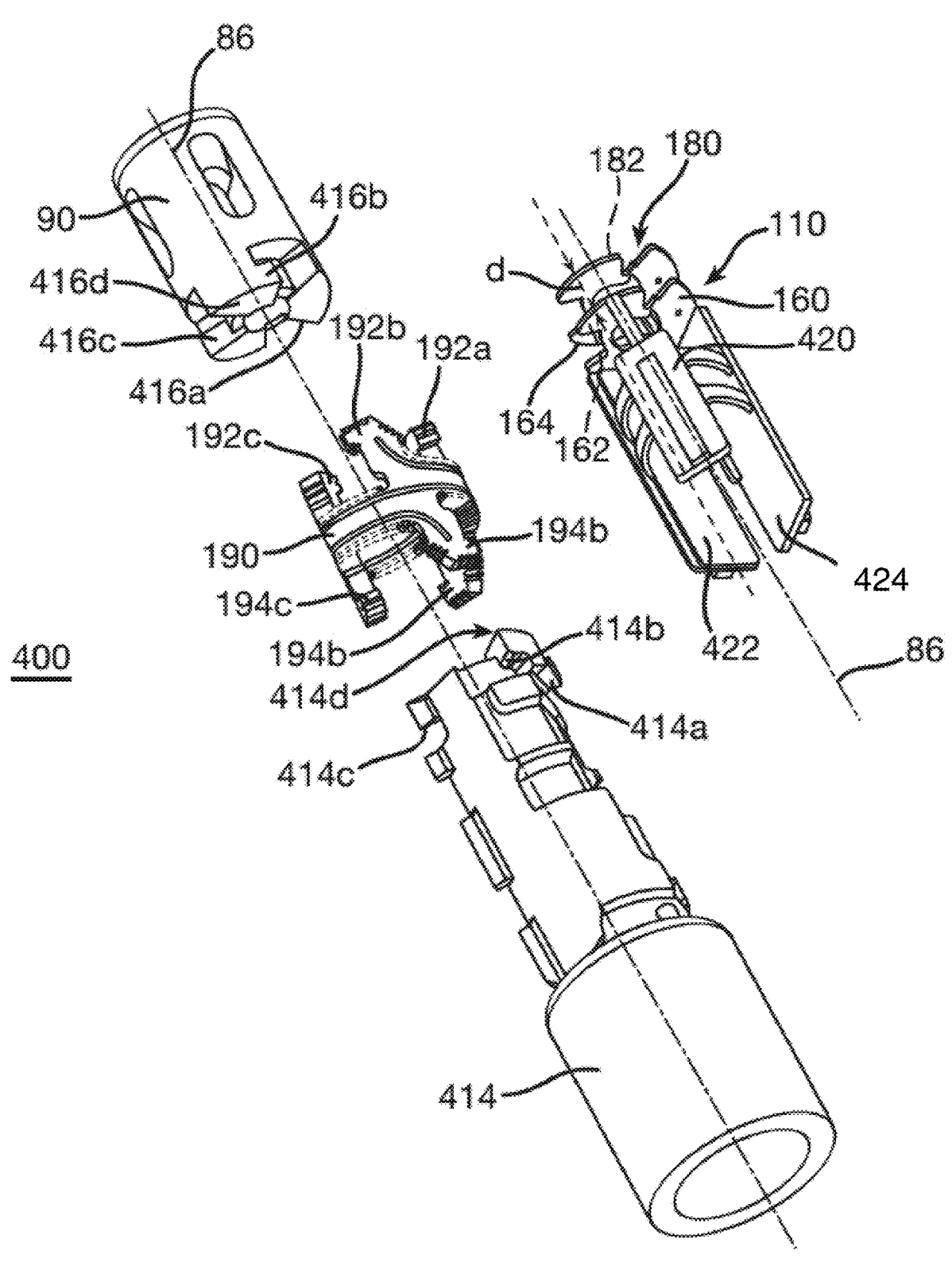
FIG. 2D is an exploded view of the contact force sensor 400 of FIG. 2C.
Figures 3A, 3B, 4:
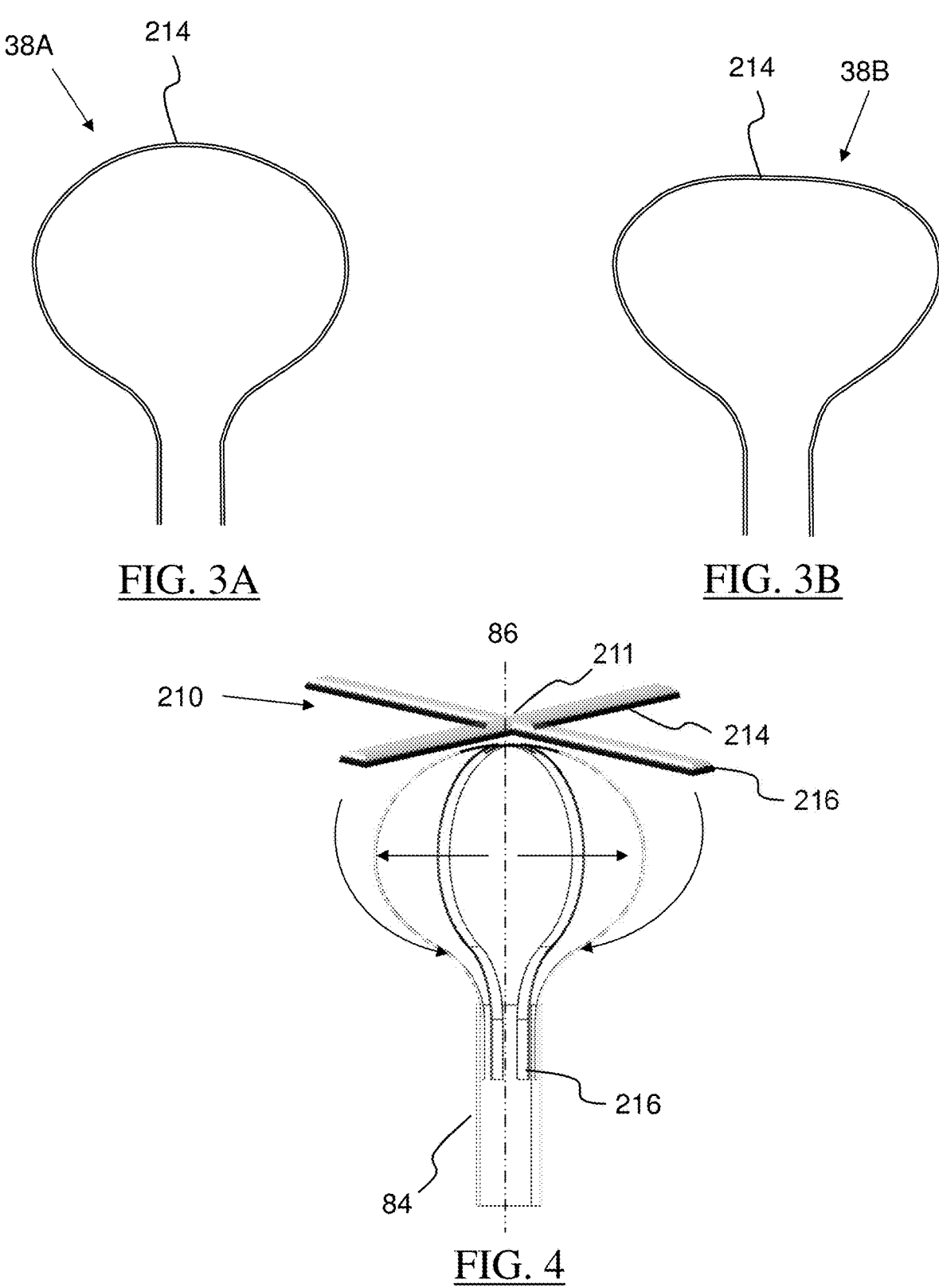
FIGS. 3A and 3B are schematic pictorial illustrations showing a profile outline of a basket assembly of a given medical device, in accordance with embodiments of the present invention.
FIG. 4 is a schematic pictorial illustration showing a side view of a plurality of linear spines forming a basket assembly, in accordance with an embodiment of the present invention.

The medical probe 22 can include a guide sheath and a therapeutic catheter, wherein the guide sheath includes the flexible insertion tube 30 and the handle 32 and the therapeutic catheter includes the basket assembly 38, electrodes 40, and a tubular shaft 84 (see FIGS. 2 through 4). The therapeutic catheter is translated through the guide sheath so that the basket assembly 38 is positioned in the heart 26. The distal end 36 of the medical probe 22 corresponds to a distal end of the guide sheath when the basket assembly 38 is contained within the flexible insertion tube 30, and the distal end 36 of the medical probe 22 corresponds to a distal end of the basket assembly 38 when the basket assembly 38 is extended from the distal end of the guide sheath. The medical probe 22 can be alternatively configured to include a second handle on the therapeutic catheter and other features as understood by a person skilled in the pertinent art.

In the configuration shown in FIG. 1, control console 24 is connected, by a cable 42, to body surface electrodes, which typically include adhesive skin patches 44 that are affixed to patient 28. Control console 24 includes a processor 46 that, in conjunction with a tracking module 48, determines location coordinates of distal end 36 inside heart 26. Location coordinates can be determined based on electromagnetic position sensor output signals provided from the distal portion of the catheter when in the presence of a generated magnetic field. Location coordinates can additionally, or alternatively be based on impedances and/or currents measured between adhesive skin patches 44 and electrodes 40 that are affixed to basket assembly 38. In addition to being used as location sensors during a medical procedure, electrodes 40 may perform other tasks such as ablating tissue in the heart.

As described hereinabove, in conjunction with tracking module 48, processor 46 may determine location coordinates of distal end 36 inside heart 26 based on impedances and/or currents measured between adhesive skin patches 44 and electrodes 40. Such a determination is typically after a calibration process relating the impedances or currents to known locations of the distal end has been performed. While embodiments presented herein describe electrodes 40 that are preferably configured to deliver IRE ablation energy to tissue in heart 26, configuring electrodes 40 to deliver any other type of ablation energy to tissue in any body cavity is considered to be within the spirit and scope of the present invention. Furthermore, although described in the context of being electrodes 40 that are configured to deliver IRE ablation energy to tissue in the heart 26, one skilled in the art will appreciate that the disclosed technology can be applicable to electrodes used for mapping and/or determining various characteristics of an organ or other part of the patient's 28 body.

Processor 46 may include real-time noise reduction circuitry 50 typically configured as a field programmable gate array (FPGA), followed by an analog-to-digital (A/D) signal conversion integrated circuit 52. The processor can be programmed to perform one or more algorithms and uses circuitry 50 and circuit 52 as well as features of modules to enable the medical professional 34 to perform the IRE ablation procedure.

Control console 24 also includes an input/output (I/O) communications interface 54 that enables control console 24 to transfer signals from, and/or transfer signals to electrodes 40 and adhesive skin patches 44. In the configuration shown in FIG. 1, control console 24 additionally includes an IRE ablation module 56 and a switching module 58.

IRE ablation module 56 is configured to generate IRE pulses including peak power in the range of tens of kilowatts. In some examples, the electrodes 40 are configured to deliver electrical pulses including a peak voltage of at least 900 volts (V). The medical system 20 performs IRE ablation by delivering IRE pulses to electrodes 40. Preferably, the medical system 20 delivers biphasic pulses between electrodes 40 on the spine. Additionally, or alternatively, the medical system 20 delivers monophasic pulses between at least one of the electrodes 40 and a skin patch.

In order to dissipate the heat and to improve the efficiency of the ablation process, system 20 supplies irrigation fluid (e.g., a saline solution) to distal end 36 and to the electrodes 40 via a channel (not shown) in tubular shaft 84 (see FIGS. 2A through 2C). Additionally, or alternatively, irrigation fluid can be supplied through the flexible insertion tube 30. Control console 24 includes an irrigation module 60 to monitor and control irrigation parameters, such as the pressure and the temperature of the irrigation fluid. It is noted that while the preference for the exemplary embodiments of the medical probe is for IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

Based on signals received from electrodes 40 and/or adhesive skin patches 44, processor 46 can generate an electroanatomical map 62 that shows the location of distal end 36 in the patient's body. During the procedure, processor 46 can present map 62 to medical professional 34 on a display 64, and store data representing the electroanatomical map in a memory 66. Memory 66 may include any suitable volatile and/or non-volatile memory, such as random-access memory or a hard disk drive.

In some embodiments, medical professional 34 can manipulate map 62 using one or more input devices 68. In alternative embodiments, display 64 may include a touchscreen that can be configured to accept inputs from medical professional 34, in addition to presenting map 62.

FIG. 2A is a schematic pictorial illustration showing a perspective view of a medical probe 22 including a basket assembly 38 in an expanded form when unconstrained, such as by being advanced out of an insertion tube lumen 80 (FIG. 2B) at a distal end 36 of an insertion tube 30 (FIG. 2B). The medical probe 22 illustrated in FIG. 2A lacks the guide sheath illustrated in FIG. 1. FIG. 2B shows the basket assembly in a collapsed form within insertion tube 30 of the guide sheath. In the expanded form (FIG. 2A), spines 214 bow radially outwardly and in the collapsed form (FIG. 2B) the spines are arranged generally along a longitudinal axis 86 of insertion tube 30.

As shown in FIG. 2A, basket assembly 38 includes a plurality of flexible spines 214 that are formed at the end of a tubular shaft 84 and are connected at both ends. During a medical procedure, medical professional 34 can deploy basket assembly 38 by extending tubular shaft 84 from insertion tube 30 causing basket assembly 38 to exit insertion tube 30 and transition to the expanded form. Spines 214 may have elliptical (e.g., circular) or rectangular (that may appear to be flat) cross-sections, and include a flexible, resilient material (e.g., a shape-memory alloy such as nickel-titanium, also known as Nitinol) forming a strut as will be described in greater detail herein.

As shown in FIG. 2A, the plurality of flexible linear spines 214 converge at a central spine intersection 211. In some examples central spine intersection 211 can include one or more cutouts 212 that allow for bending of the spines 214 when each spine respective attachment end 216 (FIG. 2C) is connected to the spine retention hub 90 which may include a flow diverter for irrigation fluid, described in more detail below.

In embodiments described herein, one or more electrodes 40 positioned on spines 114 of basket assembly 38 can be configured to deliver ablation energy (RF and/or IRE) to tissue in heart 26. Additionally, or alternatively, the electrodes can also be used to determine the location of basket assembly 38 and/or to measure a physiological property such as local surface electrical potentials at respective locations on tissue in heart 26. The electrodes 40 can be biased such that a greater portion of the one or more electrodes 40 face outwardly from basket assembly 38 such that the one or more electrodes 40 deliver a greater amount of electrical energy outwardly away from the basket assembly 38 (i.e., toward the heart 26 tissue) than inwardly. Electrodes 40 are coupled to the spine 214 via electrode inserts 300 that can be bonded or fused to spines 214 while holding electrodes 40 in a fixed position on the spine 214.

As shown in FIG. 2A, a spine 214 is shown with one electrode 40 hidden so that electrode inserts can be seen. Inserts 300 can be made from an insulative material to insulate or isolate electrode 40 from contact or conduction with spine 214. The material for insert 300 can be any suitable insulative biocompatible material as long as such material can withstand at least 1900 Volts with at least 20 amperes of current. The spines may also be provided with an insulative cover 302 of a biocompatible polymer such as, for example, polyurethane to further insulate or isolate spines 214 from contact with body tissues or fluids. The insert holder 300 can be bonded directly to the 302 or spine 214 and subsequently further bonded to the insulative spine covers 302.

Examples of materials ideally suited for forming electrodes 40 include gold, platinum and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 26.

Basket assembly 38 has a distal end 39. The medical probe 22 can include a spine retention hub 90 that extends longitudinally from a distal end of tubular shaft 84 towards distal end 39 of basket assembly 38. As described supra, control console 24 includes irrigation module 60 that delivers irrigation fluid to basket assembly 38 through tubular shaft 84.

Turning to FIG. 2C, basket assembly 38 includes a single unitary structure that includes a plurality of linear spines 214 formed from a planar sheet of material 910 (shown more clearly in FIGS. 3 and 4A). The spines 214 may be concealed and covered by at least one or more extrusion layers 80, which electrode 40 are disposed around. The one or more extrusion layer 70, 80 may include two halves connect to each other and enable be placed around each spin 214. In other embodiments, the one or more extrusion layers 80 may be overmolded on each spine 214 or over end portions of each spine 214 as is the case for extrusion layers 70. The spine retention hub 90 can be inserted into the tubular shaft 84 and attached to the tubular shaft 84. Spine retention hub 90 can include a cylindrical member 94 including a plurality of relief lands 96, an upper portion 97, and multiple irrigation openings 98 positioned about the upper portion 97, and at least one spine retention hub electrode 99, or some combination thereof. Relief lands 96 can be disposed on the outer surface of cylindrical member 94 and configured to allow a portion of each spine 214, such as each spine attachment end 216, to be fitted into a respective relief land 96 and attached/locked via an attachment end hole 216*a* and an attachment end neck 216*b*. The attachment end 216 can be a generally linear end of the spine 214. The attachment end 216 can be configured to extend outwardly from the spine retention hub 90 such that the basket assembly 38 is positioned outwardly from the spine retention hub 90 and, consequently, outwardly from the tubular shaft 84. In this way, the spine 214 can be configured to position the basket assembly 38 distally from the distal end of the tubular shaft 84 and distal from the distal end of the insertion tube 30 when the basket assembly is deployed.

As described supra, control console 24 includes irrigation module 60 that delivers irrigation fluid to distal end 36. The multiple irrigation openings 98 can be angled to spray or otherwise disperse of the irrigation fluid to either a given electrode 40 or to tissue in heart 26. Since electrodes 40 do not include irrigation openings that deliver irrigation fluid, the configuration described hereinabove enables heat to be transferred from the tissue (i.e., during an ablation procedure) to the portion of the electrodes on the inner side of the spines 214, and the electrodes 40 can be cooled by aiming the irrigation fluid, via irrigation openings 98, at the portion of the electrodes 40 on the inner side of the spines 214. Spine retention hub electrode (usable as a reference electrode) 99 disposed at a distal end of retention hub 90 can be used in combination with electrodes 40 on the spines 214, or alternatively, can be used independently from electrodes 40 for reference mapping or ablation.

FIG. 2D is an exploded view for contact force sensor 400 referenced in FIG. 2C. As shown in FIG. 2D, the contact force sensor 400 is disposed inside tube 84 and proximally in relation to the basket assembly 38 and as close as possible to the basket 38 so that contact with cardiac tissue by the spines 214 can be transmitted to the contact force sensor 400. Contact force sensor 400 includes coupler 414 provided with a plurality of notches 414*a*, 414*b*, 414*c* on the periphery of the cylindrical member or coupler 414 for corresponding engagement with protrusions 194*a*, 194*b*, 194*c* of beam coupling member 190. A spine retention hub or coupler 96 is provided with notches 416*a*, 416*b*, 416*c* that mates with protrusions 192*a*, 192*b*, 192*c* of beam coupling member 190. Flat surfaces 416*d* (angled with respect to axis 86 for spine retention hub or coupler 96) are formed whereby each flat surface 416d is angulated with respect to the axis 86 so that each flat surface is complementary to the angulation 190 defined by the helicoid path of ramp 194a, 194b, 194c (i.e., helix angle). Three flat surfaces (not shown due to the perspective view) 414d are also provided for coupler 414 in a configuration similar to flat surface 416d of spine retention hub or coupler 96 in that the three flat surfaces 414d are also angulated with respect to the axis 86 so that each flat surface 414d of coupler 414 are generally parallel to the angulation path 190 defined by the helicoid ramp 194a, 194b, 194c as well as flat surface 416d.

The location sensor coils 422 and 424 are mounted to a coupler 414 (for coupling with hub 96) in a generally equiangular configuration about the axis 86. Coupler 414 is disposed inside of tubular shaft 84 towards a proximal portion of the catheter. It is noted that while two coils (for X and Y axes in the cartesian XYZ coordinate) are used in an exemplary embodiment to determine the location of these coils (as mounted to the coupler 414 and thereby the location of the basket spines as the distance between basket spines and the location sensor is known), in certain circumstances, only one location sensing coil may be utilized if the other two axes are known via other visualization techniques. As well, three location sensing coils may also be used depending on the packaging constraints of the catheter.

Each of the trefoil force sensor segment 160, 162, 164 for flex circuit 110 is mounted in the beam coupling member 190 such that each segment 160, 162, 164 has a counterpart segment with flex circuit 180. For example, segment 162 of flex circuit 110 is mounted to be parallel to segment 182 of flex circuit 180 at a specified distance "d" (which distance "d" can change when forces are applied to coupler 90 or 414). The remainder of the force sensor coil segments 162 and 164 of flex circuit 110 are mounted in a similar manner with the respective trefoil force sensor segment of flex circuit 180. Displacement for each pair of trefoil force sensor segment will allow console 24 to determine the angle and direction of forces being applied to which one of the pie-shaped force sensor coil segment pairs. For example, when distance "d" (opposite facing arrows in FIG. 2D) between force sensor coil segments 162 and 182 is changed without the distance on the other two pair of force sensor coil segments being changed, then the processor of the system is able to determine that a force is being applied along one of the directions designated by the dual-facing arrow (FIG. 2D).

Details of the contact force sensor are provided in US Patent Application Publication No. US20210077180A1 published Mar. 18, 2021, which disclosure is incorporated by reference herein.

FIGS. 3A and 3B are schematic pictorial illustrations showing a profile outline of a basket assembly 38A, 38B such that when the basket assembly is deployed the spines define a three-dimensional shape including the profile. The basket assembly can be approximately spheroid including an approximately circular profile as shown in FIG. 3A. The basket assembly can have an approximately oblate-spheroid shape including an approximately elliptical profile as shown in FIG. 3B. Although not every variation of shape is shown or described herein, one skilled in the art will appreciate that spines 214 can be further configured to form other various shapes as would be suitable for the particular application.

By including spines 214 configured to form various shapes when in the expanded form, basket assembly 38 can be configured to position the various electrodes 40 attached to spines 214 at various locations, with each location being nearer or farther from the distal end of tubular shaft 84. For example, electrode 40 attached to spine 214 illustrated in FIG. 3A near the middle of spine 214 would be farther from the distal end of tubular shaft 84 than spine 214 illustrated in FIG. 3B when basket assembly 38 is in the expanded form. In addition, each spine 214 may have an elliptical (e.g., circular) or rectangular (that may appear to be flat) cross-section, and include a flexible, resilient material (e.g., a shape-memory alloy such as nickel-titanium (also known as Nitinol), cobalt chromium, or any other suitable material).

Figures 5A, 5B:
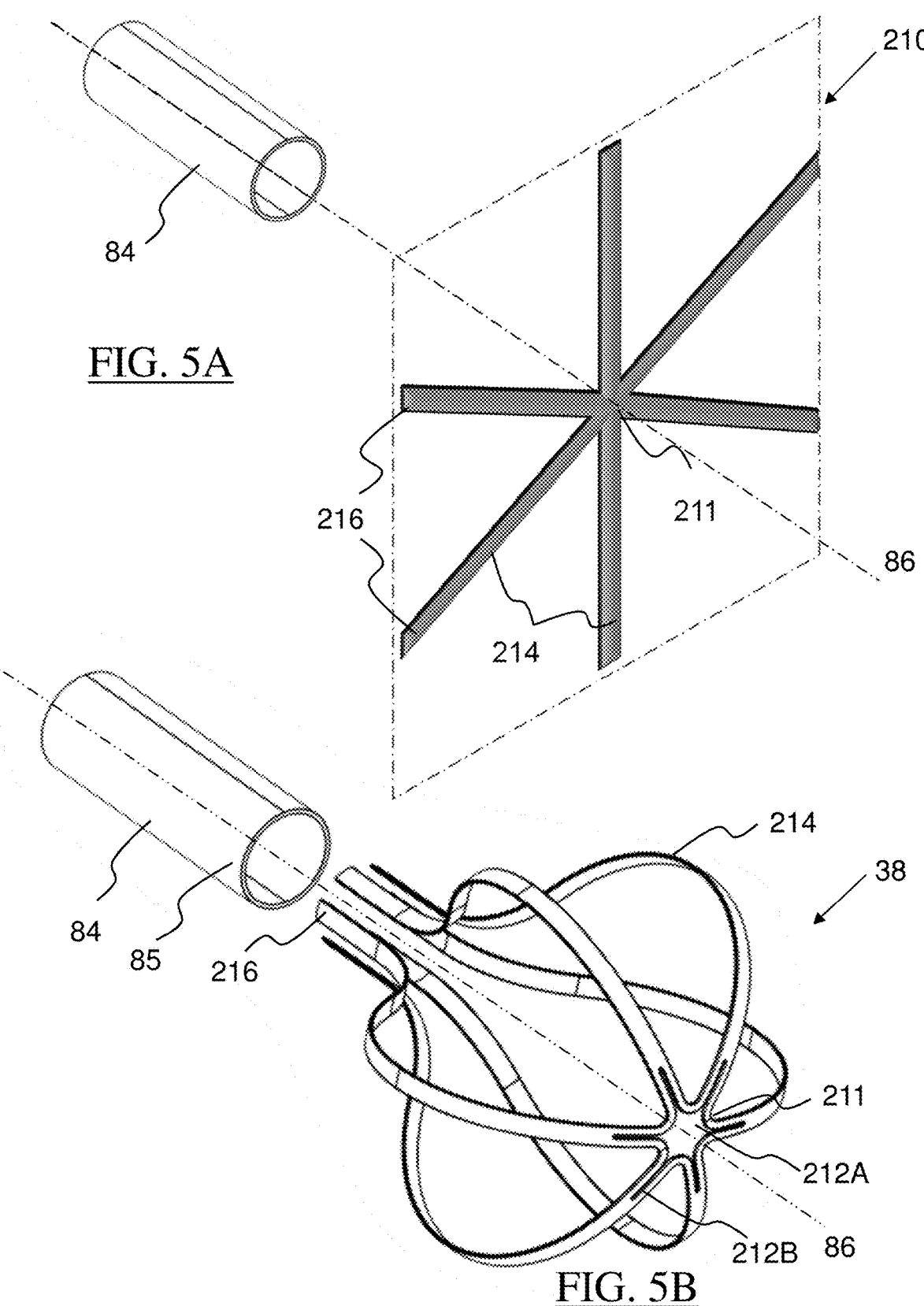
FIGS. 5A and 5B are schematic pictorial illustrations of a method of forming a basket assembly, in accordance with an embodiment of the present invention.

FIGS. 4, 5A and 5B are schematic pictorial illustrations showing views of spines 214 forming basket assembly 38. FIG. 4 provides one example of how planar sheet of material 910 may be assembled together with tubular shaft 84 whereby each spine 214 bends or curves when respective attachment ends 216 are connected to spine retention hub 90. As shown in FIG. 5A, the spines 214 can be formed from a single sheet of planar material 910 to form a generally star shape. In other words, spines 214 can be formed from the single sheet of planar material such that the spines 214 converge toward a central spine intersection 211. The intersection 211 can be a solid piece of material (as shown in FIG. 5A) or include one or more cutouts 212 (as shown in FIG. 5B). Basket assembly 38 can include a number of spines 214 ranging from about four to about ten spines from a single sheet of planar material 910.

Figure 5C:
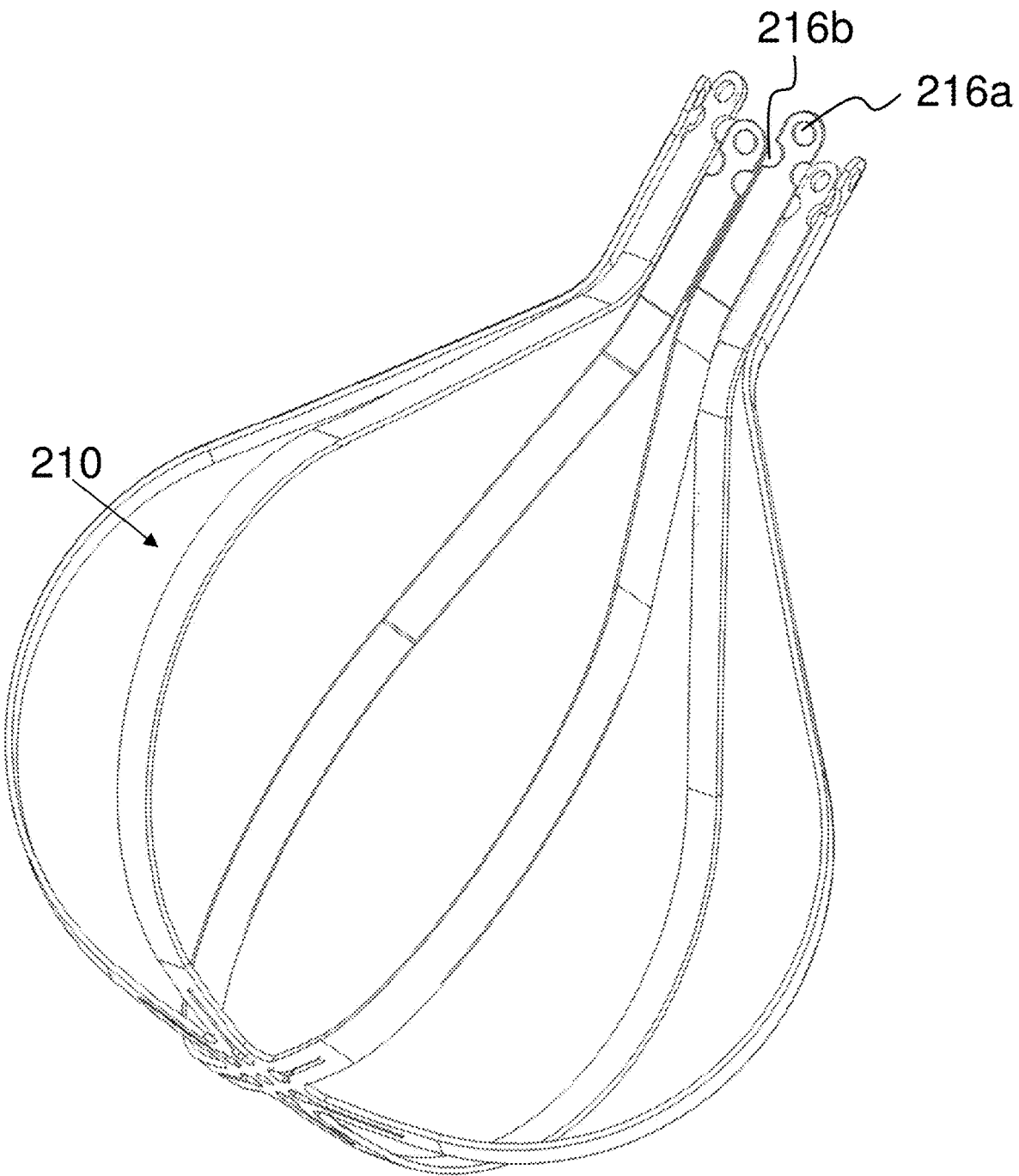
FIG. 5C illustrates an embodiment where the proximal end of each spine is provided with a hole and reference notches to ensure correct alignment and retention of the spine to the irrigation tube, in accordance with an embodiment of the present invention.
Figure 5D:
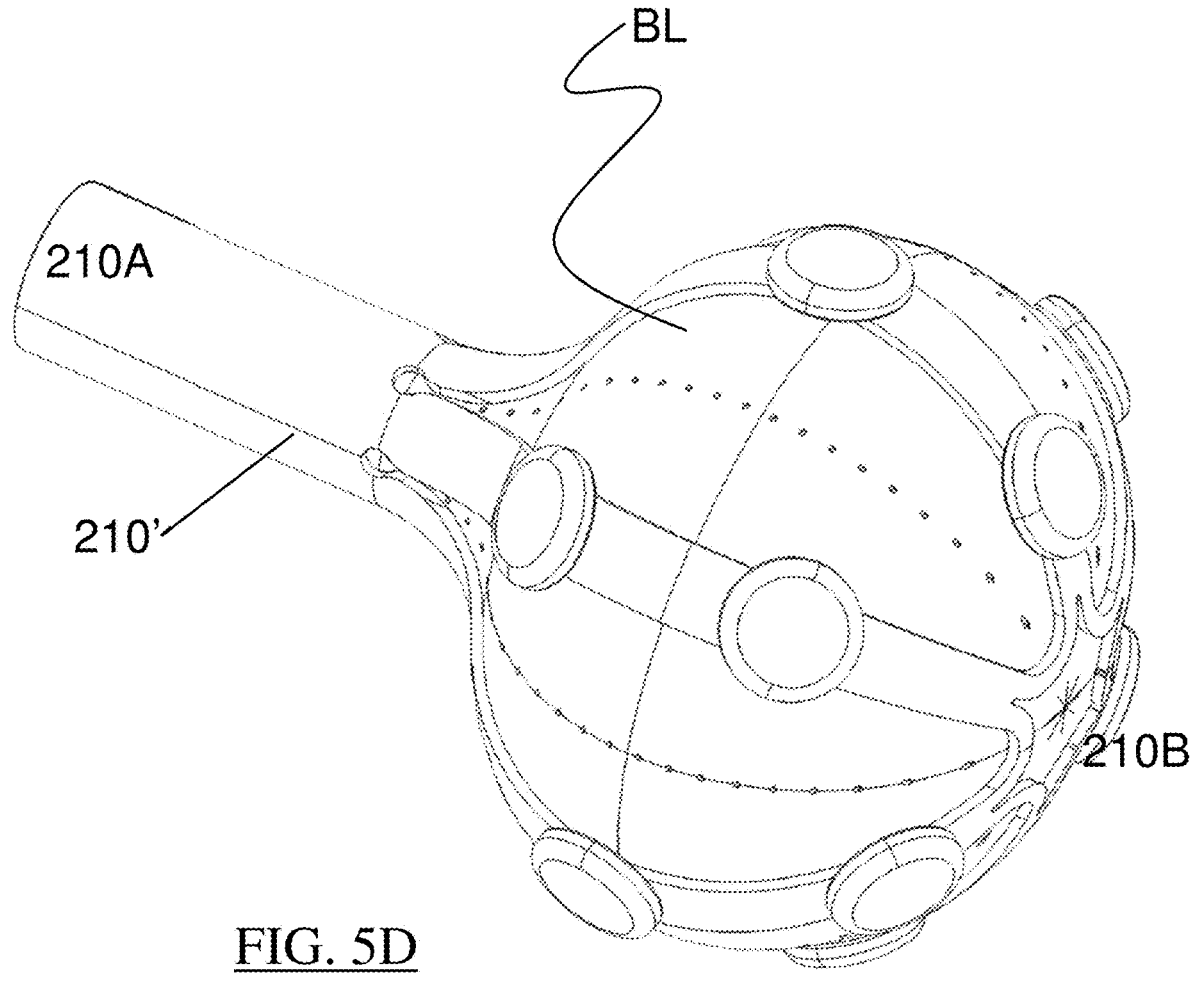
FIG. 5D illustrates an embodiment that relies on a balloon to expand the spine assembly, in accordance with an embodiment of the present invention.

The spine assembly 210 can be physically connected to the tubular member 84 via a suitable technique such as adhesive or molding. In one embodiment shown here in FIG. 5C, eyelet 216a as well as locators 216b can be provided to aid in assembly as well as physical retention of the spines to the tubular member 84.

Where it is desired, a balloon BL can be provided as shown in FIG. 5D inside the spine assembly 210' to ensure full expansion of the spine assembly 210' from a cylindrical form factor into a spheroidal form as shown in FIG. 5C.

Figure 5E:
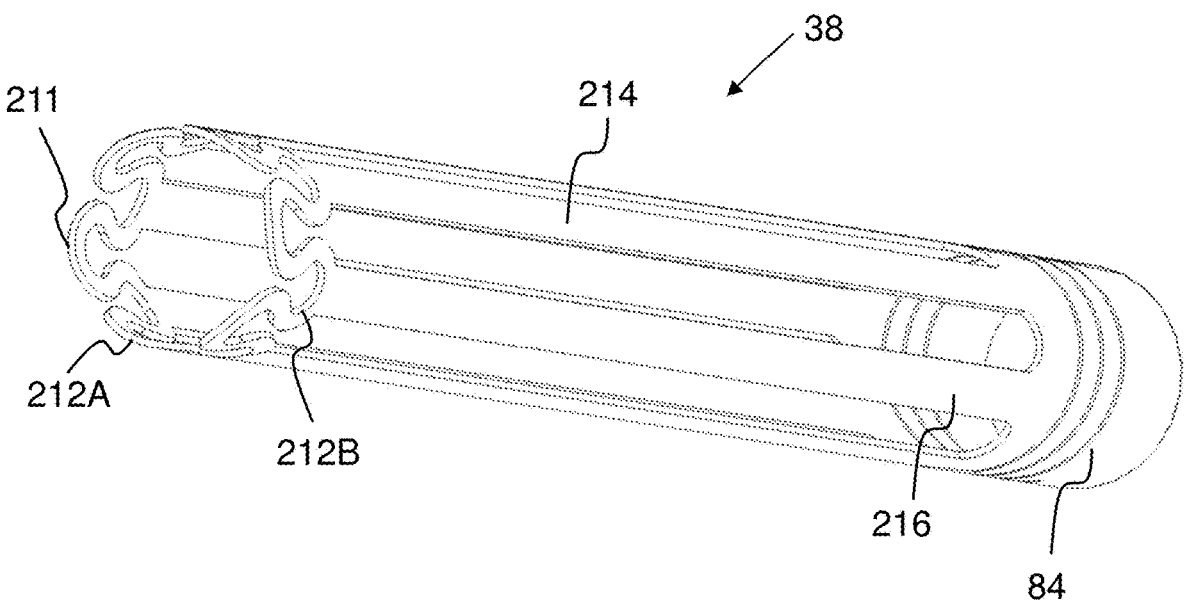
FIG. 5E illustrates a spine assembly formed by cutting a cylindrical tube stock with a laser, in accordance with an embodiment of the present invention.
Figure 5F:
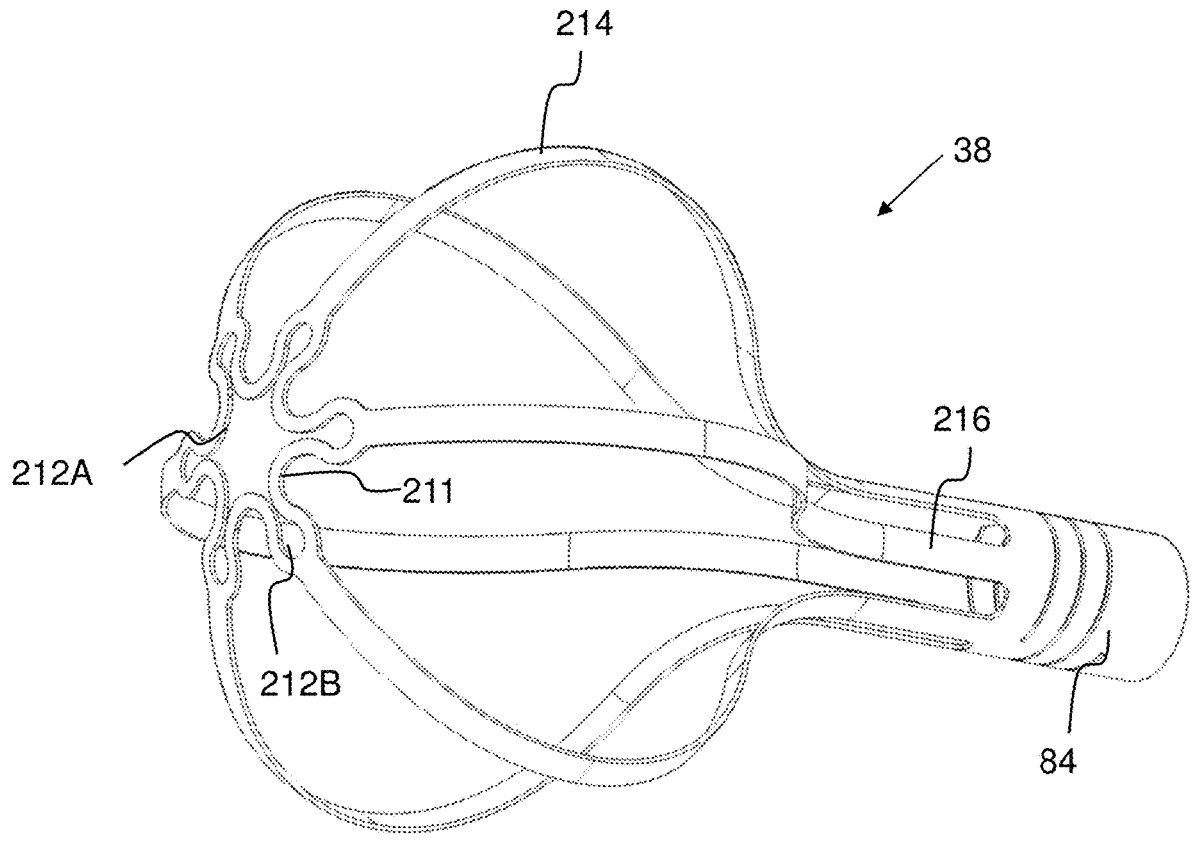
FIG. 5F illustrates a spine assembly after shape setting of the spines in FIG. 5E into a spheroidal basket like shape, in accordance with an embodiment of the present invention.
Figure 5G:
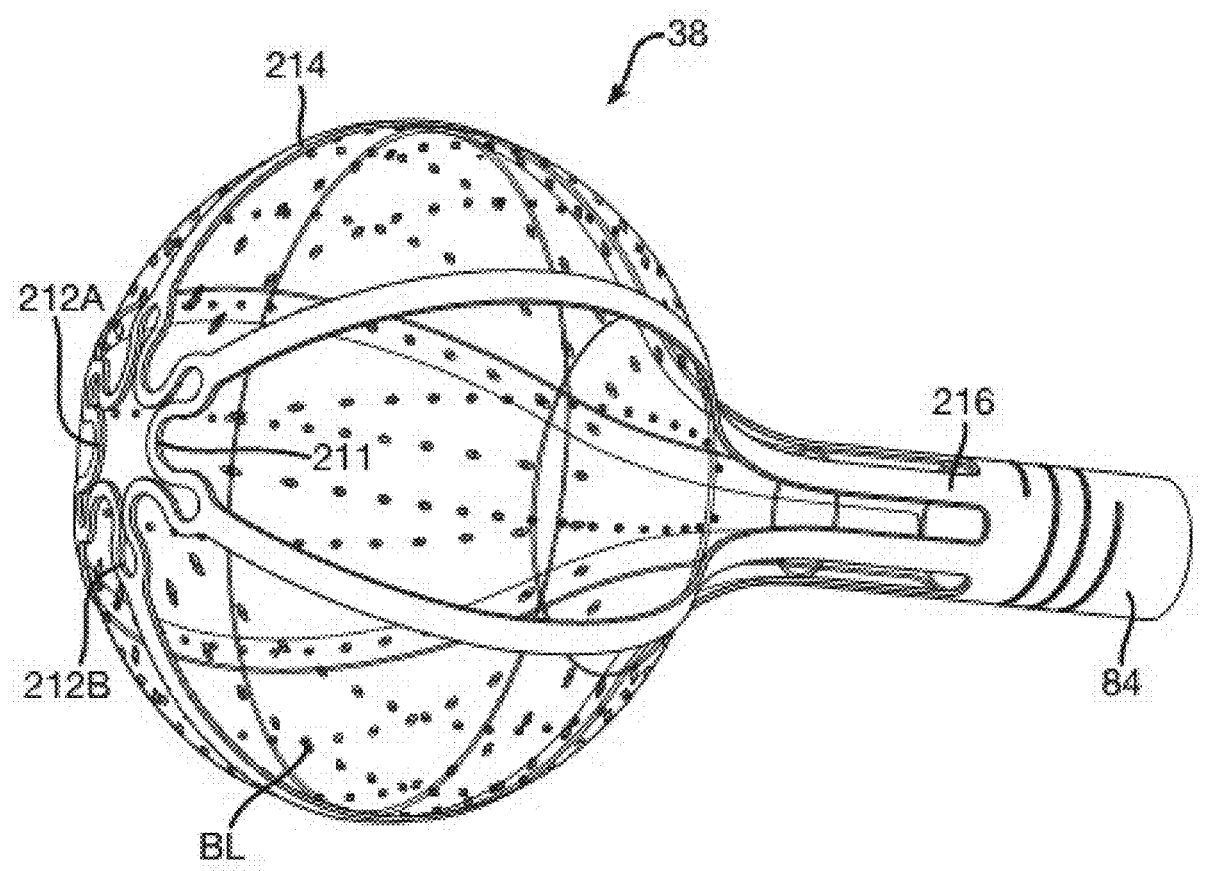
FIG. 5G illustrates a spine assembly of FIG. 5F that relies on a balloon to expand the spine assembly.

The spine assembly can be made from a tubular cylindrical stock material so that the proximal portion 210A and distal portion 210B are of one-piece material. The tubular stock is cut into a desired shape for the spine assembly 210' as shown in FIG. 5E. Thereafter, the cut tube can be shape set (or heat set) as is known by those skilled in the art to provide for the spheroidal spine configuration shown in FIG. 5F. When cut from tubular cylindrical stock material, the expandable basket assembly 38 may be also include a tubular shaft 84 which is formed with the spines 214 as shown in FIG. 5F and do not have to be attached since they are connected as one piece. Much like FIG. 5D an expandable basket assembly 38 formed from tubular cylindrical stock material may retain a balloon BL to ensure full expansion of the spine assembly 38 as shown in FIG. 5G.

Figure 6A:
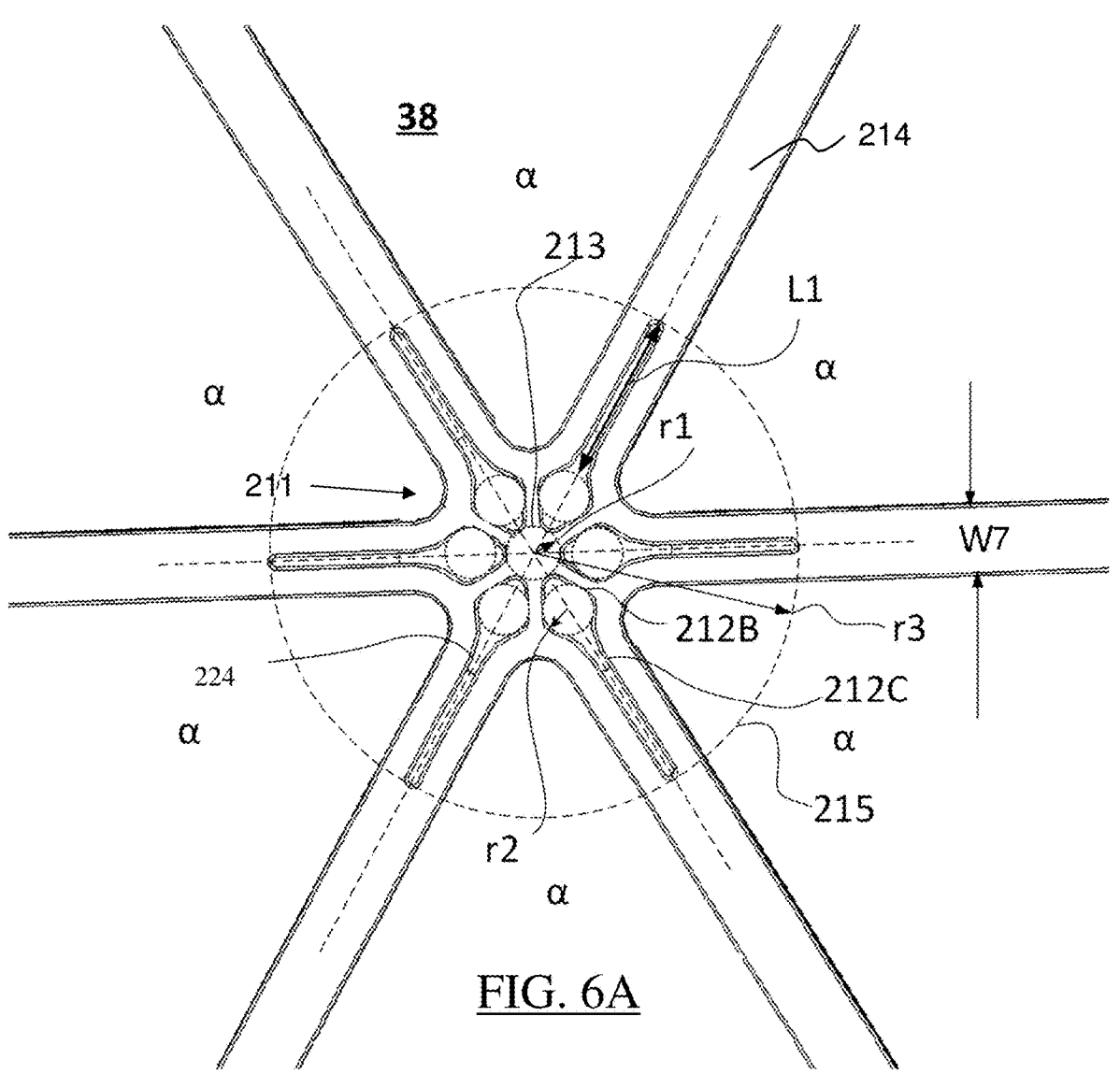
Figure 6B:
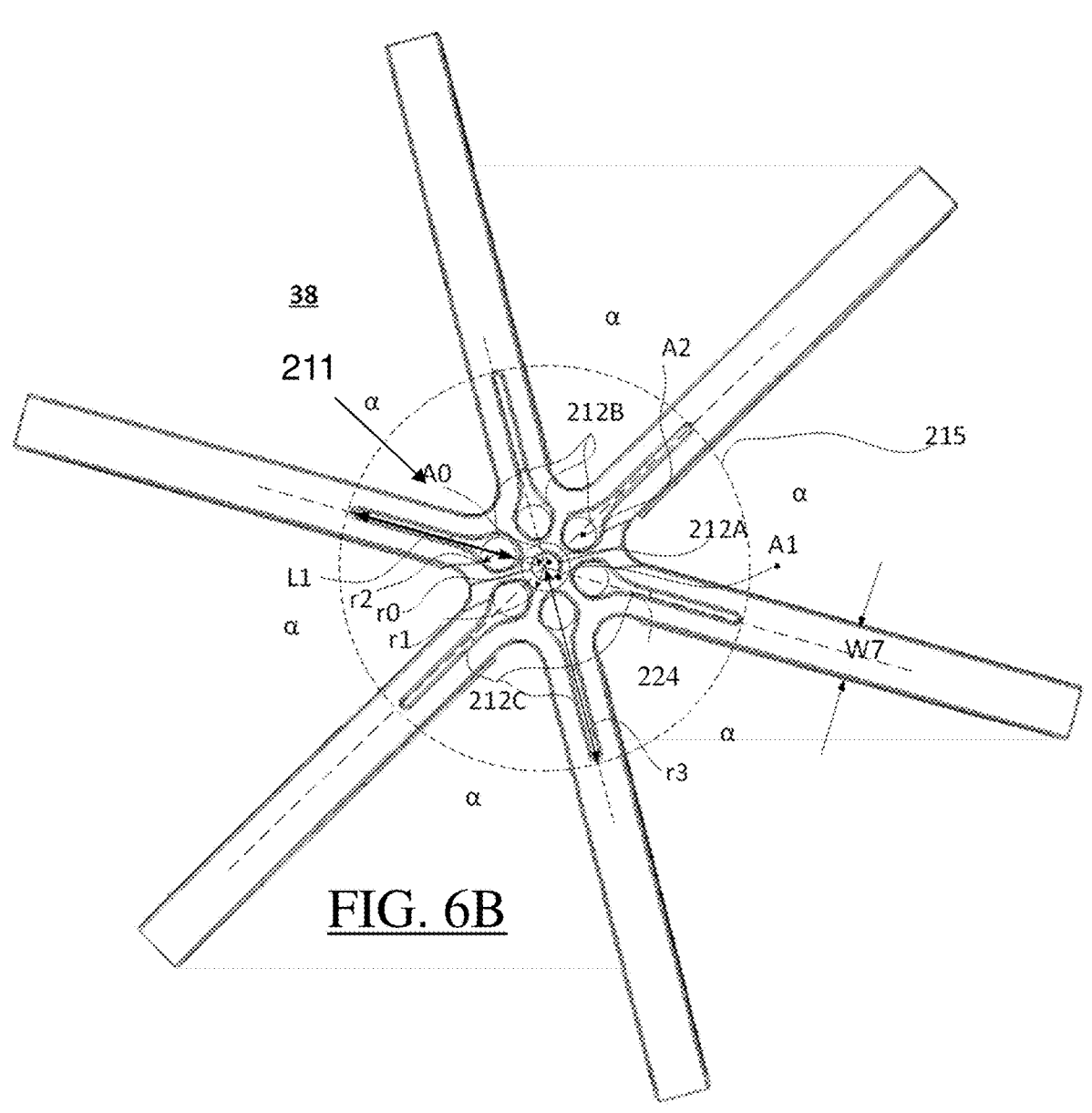
Figure 6C:
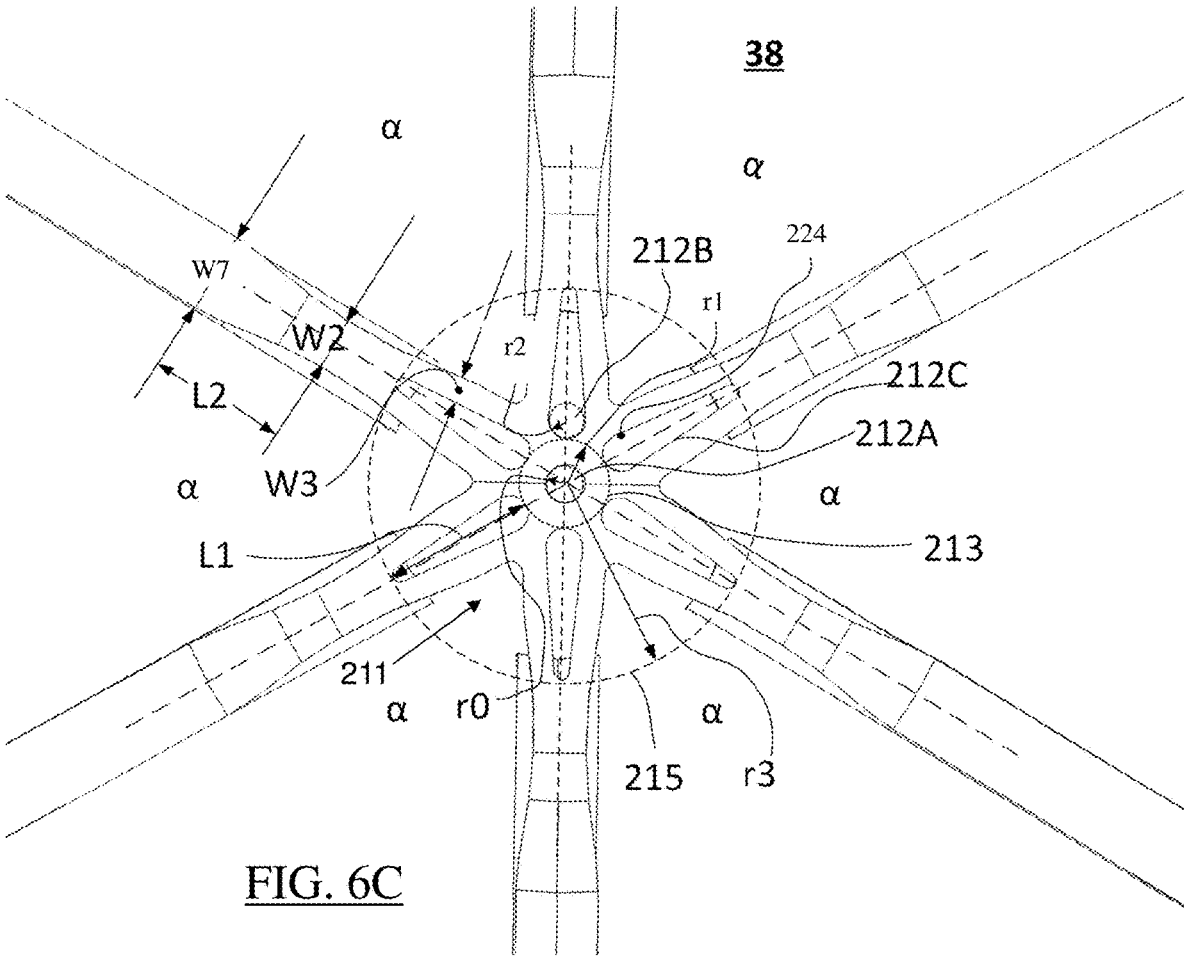
Figure 6D:
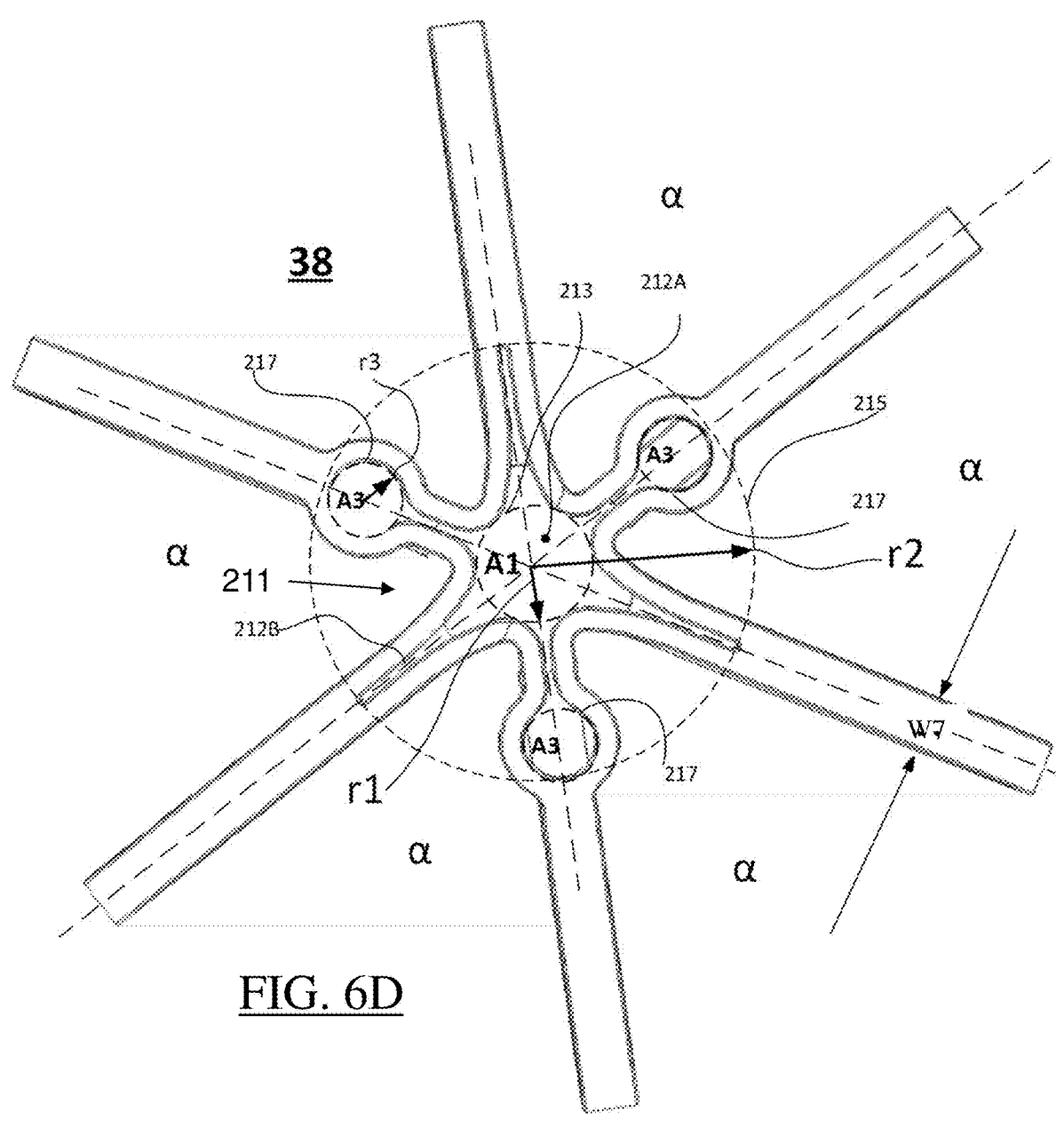

FIGS. 6A through 6K are schematic pictorial illustrations of top-down views of expandable basket assembly 38, showing various examples of one or more cutouts 212 on central spine intersection 211. As shown, intersection 211 can include a single discrete cutout as shown, for example in FIGS. 6D, 6G, and 6I that includes a central aperture 212A connected to radial cutouts 212B. Alternatively, intersection 211 can include two or more radial cutouts 212B, 212C with or without a central aperture cutout 212A as provided as an example in FIGS. 6A and 6B. The one or more cutouts 212A, 212B, 212C can include a variety of patterns, such as centrosymmetric (i.e., symmetric with respect to a central point), and equiangular (i.e., including equal angles) to allow for equal bending among the spines 214 as well as disproportional and asymmetric to allow for unequal bending of spines 214 to alter structural stability. In certain instances, when basket assembly 38 includes an even number of spines 214, the pattern of the one or more cutouts 212 can alter between every other spine, as illustrated in FIG. 6D. In some examples, one or more cutouts 212 can extend along a portion of each spine 214. In other examples, such as FIGS. 6J and 6K, the spines 214 may form a spiral pattern about the central spine intersection 211. Each of the designs illustrated in FIGS. 6A-6K will be discussed separately.

In FIG. 6A, the center (on axis 86) of the radiating spines 214 for basket 38 does not have a cut-out so that there is no void at the center of the basket to act as sharp edge surface (at the edge of such center aperture) against biological tissues. To allow for consistent folding of the spines near the distal portion of basket 38, each spine is provided with a tadpole shaped cutout 224 that extends from the head portion 212B to tail portion 212C. The head portions 212B are arrayed so that the head portions 212B are contiguous to an outside circumference of first virtual circle 213 with radius r1. Each head portion 212B has a negative surface area that can be approximated by a second virtual circle with radius r2 of approximately 90% of the first radius r1. The tail portions 212C are bounded by a third virtual circle 215 with a radius r3 approximately 10 times that of the first radius. The length L1 of each of the tail portion includes approximately 1.5 times that of the width W7 of the spine 214. In one exemplary embodiment (out of many), the total negative area of the six cut-outs includes approximately 1.5 mm-squared. The angle α between two adjacent spines 214 may be approximately 30 degrees to 100 degrees (e.g., approximately 60 degrees).

In FIG. 6B, this design has a small aperture 212A disposed at the center (coincident with longitudinal axis 86) of the basket 38 with a tadpole shaped cut-out 224 disposed on each of the spines 214. Each tadpole cut-out 224 is defined by an aperture cutout 212B that is merged with grooved cutout 212C. It is noted that while aperture 212A or 212B is shown approximating a circle, it is within the scope of this invention to have cut-out opening 212A or 212B in any shape as long as each aperture 212A or 212B has the requisite negative area. In the event the aperture 212A is configured as a circle, aperture 212A has central void A0 (of negative area) that can be approximated by a first virtual circle with radius r0 while each aperture 212B has a second area A2 that can be represented by a second virtual circle with radius r2. The apertures 212B (or the "heads" of the tadpole cutouts) are radially arrayed so that apertures 212B are contiguous to a first virtual circle with radius r1. The second virtual circle may have a second radius r2 of 1.2 times that of the radius r0 of the first virtual circle representing aperture 212A while the first virtual circle r1 may have radius r1 of approximately 1.5 times that of the radius of the central virtual circle r0. The tail or grooved opening 212C of the "tails" extends towards the proximal end of the basket 38 for a length L1 so that each tail is contiguous to an inside circumference of a third virtual circle 215. Slot length L1 includes approximately 6-10 times that of the first radius r1. Third virtual circle 215 may have a radius r3 extending from the longitudinal axis 86 where radius r3 includes approximately 10-15 times that of either first radius r1 or central radius r0. In the exemplary embodiment (amongst many), the negative area of each of the tadpole cutout 224 includes approximately 0.2 mm-squared while the negative area of center aperture 212A includes approximately 0.05 mm-squared so that the total negative area defined by all of the cut-outs includes approximately 1.4 mm-squared. In the same exemplary embodiment, the central radius r0 may be approximately 0.13 mm, the second radius r2 may be approximately 0.2 mm, and the first radius r1 may be approximately 0.23 mm.

In FIG. 6C, the design of the basket 38 is provided with an aperture 212A at approximate center (i.e., axis 86) of the spines 214. Each spine 214 is provided a comet-shaped cutout 224 with head portion 212B with an open tapered slot tail 212C tapering towards the proximal portion of each spine 214. The comet-shaped cut-outs 212B are arrayed so that the distal head portion 212B of the cutout 224 are contiguous to an outside circumference of second virtual circle 213 while the proximal slotted opening 212C of the cutouts 224 are contiguous on the inside circumference of third virtual circle 215. Where the aperture 212A is configured as a circular hole located on central axis 86 with radius r0 where the second radius r2 includes approximately 90% of the central radius r0, the second virtual circle 213 may have a first radius r1 of approximately 2.5 times that of central radius r0 while the third virtual circle 215 has a radius r3 of approximately 10 times that of the central radius r0 (all measured from center axis 86). Spine 214 has a width W7 that tapers towards central axis 86 to a narrower second spine width W2 of approximately 66% of width W7 at its narrowest point before being sub-divided by comet shaped cut-out 212B into two narrower spine arms with each arm including a third spine width W3 of approximately ⅓ that of the width W7. The comet shaped cut-out 212B has a length L1 along the spine of approximately 1.8 times that of the largest spine width W7.

In FIG. 6D, the basket 38 has its distal portion configured to have an open center 212A that radiates into each of the six spines 214, each approximately 60 degrees apart. The open center 212A has a first area A1 that can be approximated by a virtual circle with radius r1. Three spines approximately 120 degrees apart have tapering grooves 212B extending back toward the proximal portion of basket 38. Three other spines approximately 120 degrees apart have large apertures 217 with area A3 disposed towards the proximal portion of the basket 38. The cut-out area A3 can be approximated by a virtual circle with radius r3 and disposed on the spines 214 such that the apertures 217 are contiguous to the inside circumference of virtual circle 215 with radius r2. In this configuration, each third area A3 is about ¼ of the open first area A1 while the total negative surface area of the entire cut out includes approximately 1.6 times the first open area of empty space A1 and the second area A2 (calculated with radius r2) includes approximately 7 times the first area A1. Additionally, the second area A2 includes approximately 36 times third area A3. The radius r3 includes approximately 0.4 times that of radius r1 while radius r2 includes approximately 2.8 times that of radius r1. In one exemplary embodiment, first open area of empty space A1 includes approximately 2 mm-squared; second area A2 (as defined by radius r2) being approximately 15 mm-squared; third area A3 includes approximately 0.4 mm-squared; total area of all cut-outs includes approximately 3.5 mm-squared; radius r1~0.8 mm; r2~2.2 mm; and r3~0.4 mm.

Figure 6E:
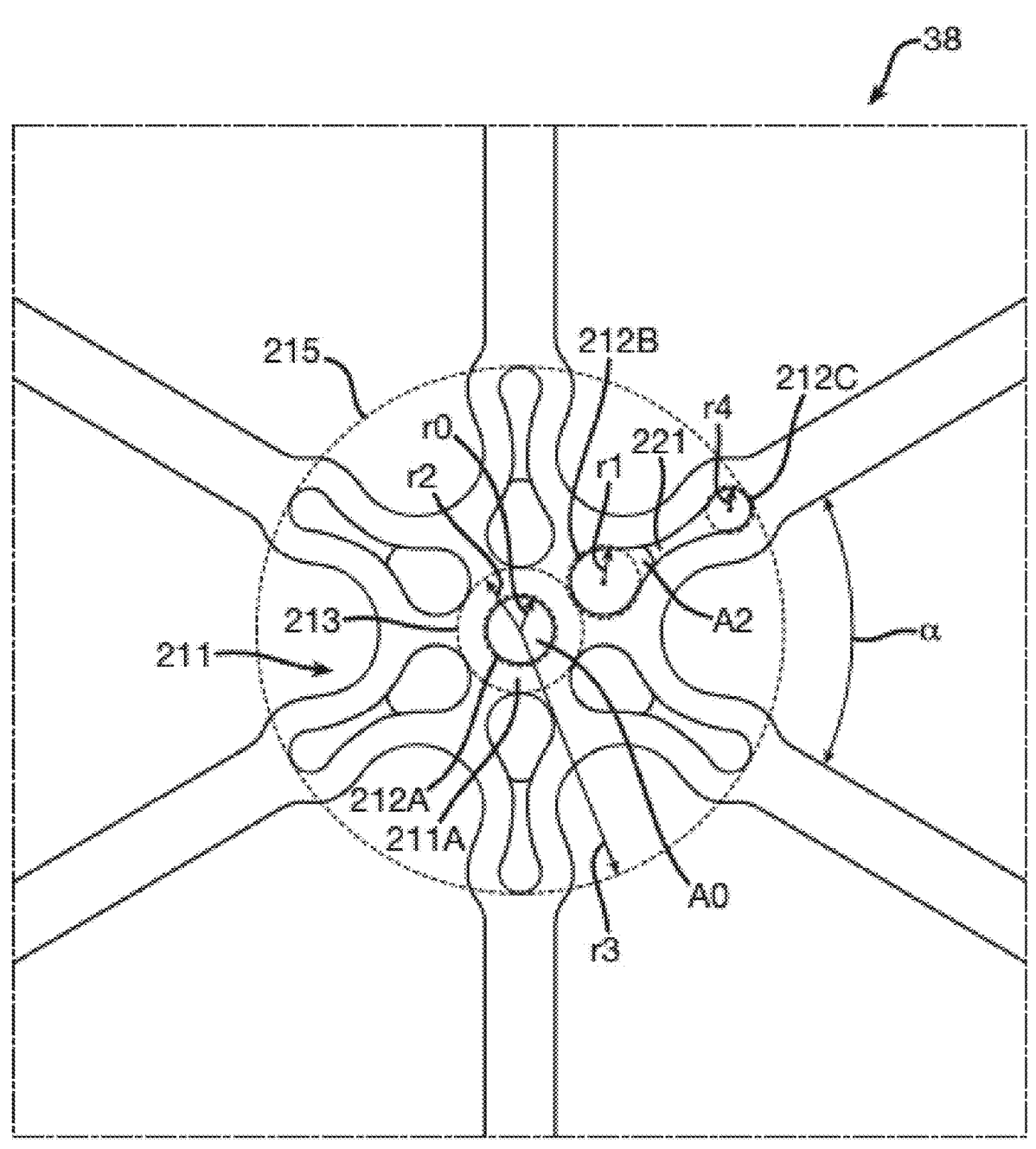

In FIG. 6E, the basket 38 may include a distal portion with an aperture 212A at approximate center (i.e., axis 86) of the spines 214 where the aperture 212A includes a radius r0 that may be about 0.13 mm to about 0.4 mm and a negative area A0 of approximately 0.01 mm-squared to approximately 0.4 mm-squared (e.g., 0.2 mm-squared). The spines 214 may be approximately 60 degrees apart at angle α and configured such that a fifth virtual circle of radius r5 is disposed between adjacent spines and the central distal portion 211A. The radius r5 of fifth virtual circle is substantially the same as the radius r1 of first virtual circle 213. The center of fifth virtual circle with radius r5 is located on an axis L bisecting the respective axes (e.g., A and B) of adjacent spines 214 (FIG. 6E1) such that any two adjacent spines 214 will have substantially the same fifth virtual circle with radius r5 disposed between them. The basket 38 may also include a plurality of hourglass cutouts 221 that extend radially along each spine 214. The hourglass cutouts 221 may include a major portion 212B at least primarily located at the central spine intersection 211 and may have a radius r1 approximately equal to the radius r0 of aperture 212A. The hourglass cutouts 221 may also include minor portion 212C located at the spines 214 which may have a radius r4 approximately half of the radius r1 of the major portion 212B. Each hourglass cutout 221 may include an area A2 of approximately 0.1 mm-squared to approximately 0.55 mm-squared (e.g., 0.39 mm squared) so that the total area of all the hourglass cutouts 221 may be 0.6 mm-squared to 3.3 mm-squared (e.g., 2.54 mm-squared). The major portions 212B are arrayed so that the major portions 212B are contiguous to an outside circumference of first virtual circle 213 with radius r1. The minor portions 212C are bounded by a third virtual circle 215 with a radius r3 approximately 10 times that of the first radius r1.

FIG. 6E1 is a variation of the embodiment shown in FIG. 6E and FIG. 6E1 uses the same nomenclatures as in FIG. 6E. In FIG. 6E1, the basket assembly does not utilize a central opening (i.e., a hole) 212A. All other features are the same as indicated by the same reference alphanumeric indicators.

FIG. 6E2 is a variation of the embodiment of FIG. 6E1 in which the cutout 212B is no longer circular but more of a snake-head like configuration referenced here as 212D. While the first virtual circle r1 can be seen disposed inside the cutout 212D, the cutout 212D elongates towards the central axis 86 such that cutout 212D would be insider the virtual circle r2 of FIG. 6E1. Cutout 212D tapers to a narrow portion and extends towards the proximal end of the assembly 38 to have the same cutout 212C disposed around the fourth virtual circle r4 with its open area as in the embodiment of FIG. 6E and FIG. 6E1.

Figure 6F:
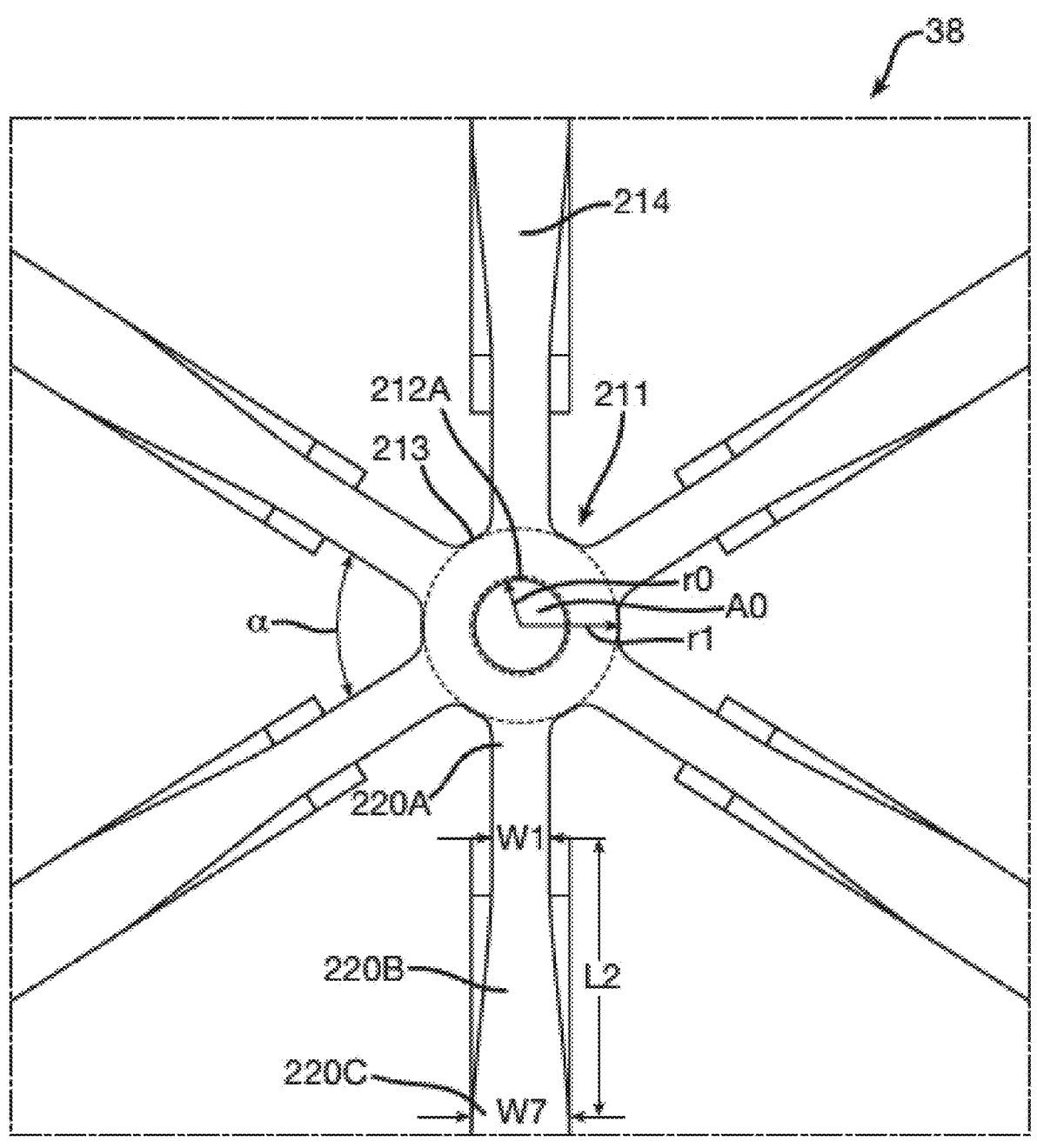

In FIG. 6F, the basket 38 may include a distal portion with an aperture 212A at the approximate center (i.e., axis 86) of the spines 214 or the central spine intersection 211 without any radial cutouts along the spines 214. The aperture 212a may include a first radius r0 approximately 0.1 mm to approximately 0.4 mm and an area A0 of approximately 0.01 mm-squared to approximately 0.4 mm-squared (e.g., preferably 0.2 mm-squared). Each spine 214 may include a first portion 220A, a second portion 220B, and a third portion 220C. The first portion 220A may include a first width W1 of approximately 0.05 mm to approximately 0.65 mm (e.g., approximately 0.26 mm). The third portion 220C may include a width W7 of approximately 0.1 mm to approximately 1.0 mm (e.g., approximately 0.56 mm) and the second portion 220B may include a tapering width narrowing from the third portion 220C to the first portion 220A with an average width of approximately 0.2 mm to approximately 0.3 mm (e.g., approximately 0.31 mm). In some embodiments, the emergence of individual spines 214 may be defined by virtual circle 213 which may have a radius r1 of approximately double that of radius r0 of the aperture 212A.

Figure 6G:
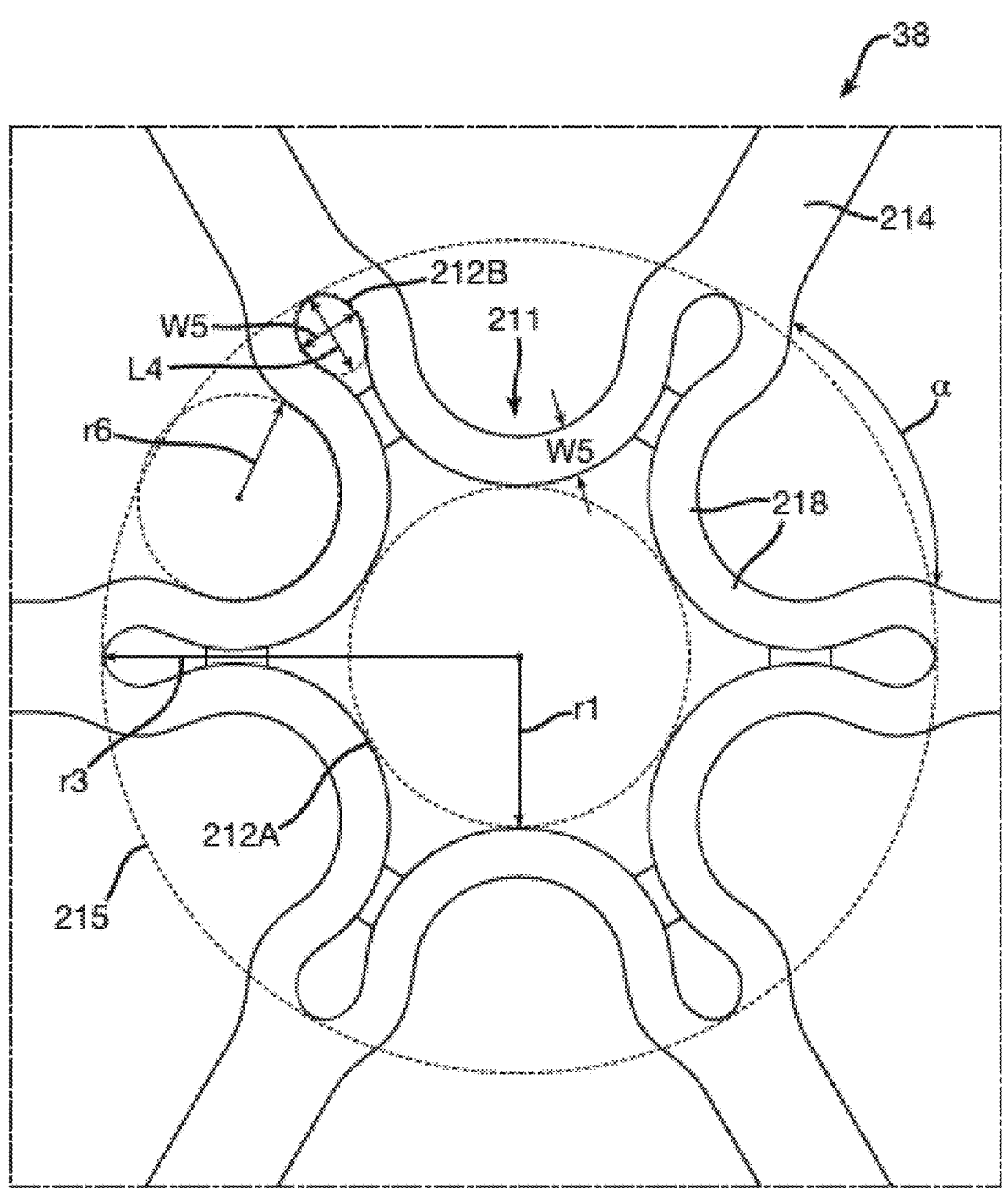

In FIG. 6G, the basket 38 may include a distal end with an aperture 212A at the approximate center (i.e., axis 86) of the spines 214 or the central spine intersection 211. Much like other embodiments, the angle α between spines 214 may be approximately 60 degrees. The aperture 212A has a radius r1 of approximately 0.4 mm to approximately 1.2 mm (e.g., approximately 0.84 mm). The basket 38 may also include a plurality of radial cutouts 212B that extend from and are connected to the aperture 212A to form a single cutout, which may result from cutting the basket 38 from tubular stock rather than planer material. Regardless, each radial cutout 212B may include an ellipse shape at an end furthest from the aperture 212A. Each ellipse-shaped radial cutout 212B may include a length L4 of approximately 0.20 mm to approximately 0.55 mm and a width W5 of approximately 0.1 mm to approximately 0.45 mm. The ellipse-shaped radial cutouts 212B may be contiguous to the inside circumference of virtual circle 215 with radius r2. In this configuration, radius r2 may be approximately 1.5 times to approximately 3 times (e.g., approximately 2.4 times) the radius r1 of the aperture. Each spine 214 may include a thickness of approximately 0.03 mm to 0.15 mm (e.g., approximately 0.09 mm). Each spine 214 may also include two connecting portions 218 that connect to adjacent spines 214 and the width W5 of each connecting portion may be approximately 0.12 mm to approximately 0.4 mm (e.g., approximately 0.24 mm). Connecting portions 218 from adjacent spines 214 may be connected and may together form a circular shape that may have a radius r6 of approximately 0.25 mm to approximately 0.75 mm (e.g., approximately 52 mm).

Figure 6H:
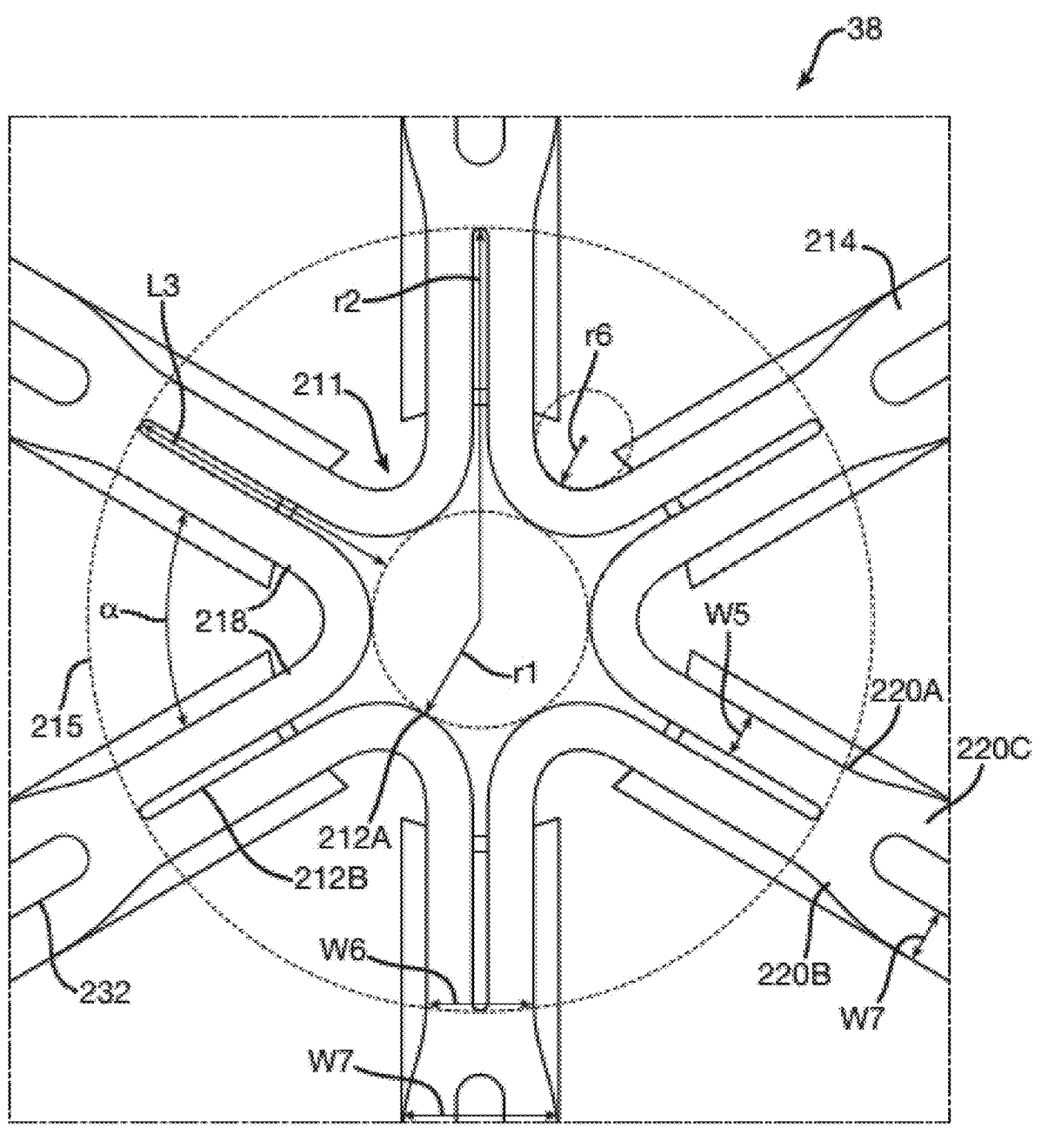

In FIG. 6H, the basket 38 may include a distal end with an aperture 212A at the approximate center (i.e., axis 86) of the spines 214 or the central spine intersection 211. Much like FIG. 6G, the angle α between spines 214 may be approximately 60 degrees, the aperture 212A may include a radius r1 of approximately 0.4 mm to approximately 1.2 mm (e.g., approximately 0.84 mm), and the basket 38 may include a plurality of radial cutouts 212B that extend from and are connected to the aperture 212A to form a single cutout, which may result from cutting the basket 38 from tubular stock rather than planer material. However, unlike FIG. 6G, the radial cutouts 212B may not include an ellipse shape and instead may be linear shaped with a length L3 of approximately 1 mm to approximately 2 mm, preferably about 1.5 mm and a generally even width but the linear struts may be tapered to distribute stresses and strains. The radial cutouts 212B may form connecting portions 218 in each spine 214 where each connecting portion 218 may have width W5 of approximately 0.12 mm to approximately 0.4 mm (e.g., approximately 0.24 mm) where the two adjacent connecting portions 218 are connected to form a circular shape between spines 214 that has a radius r6 of approximately 0.1 mm to approximately 1.1 mm (e.g., approximately 0.57 mm). The radial cutouts 212B may be contiguous to the inside circumference of virtual circle 215 with radius r2. In this configuration, radius r2 may be approximately 3.6 times the radius r1 of the aperture 212A. Each spine 214 may include the connecting portions 218, a first portion 220A with a width W6 of approximately 0.2 mm to approximately 0.9 mm (e.g., approximately 0.56 mm), a second portion 220B, and a third portion 220C with a width W7 of approximately 0.4 mm to approximately 1.2 mm (e.g., approximately 0.81 mm). The second portion 220B may have a tapering width tapers its width from width W7 to W6. Additionally, the third portion 220C of each spine may be a split spine that is split into two minor portions by slot 232, each minor portion having a width W8 of approximately 0.1 mm to approximately 0.6 mm (e.g., approximately 0.28 mm).

Figure 6I:
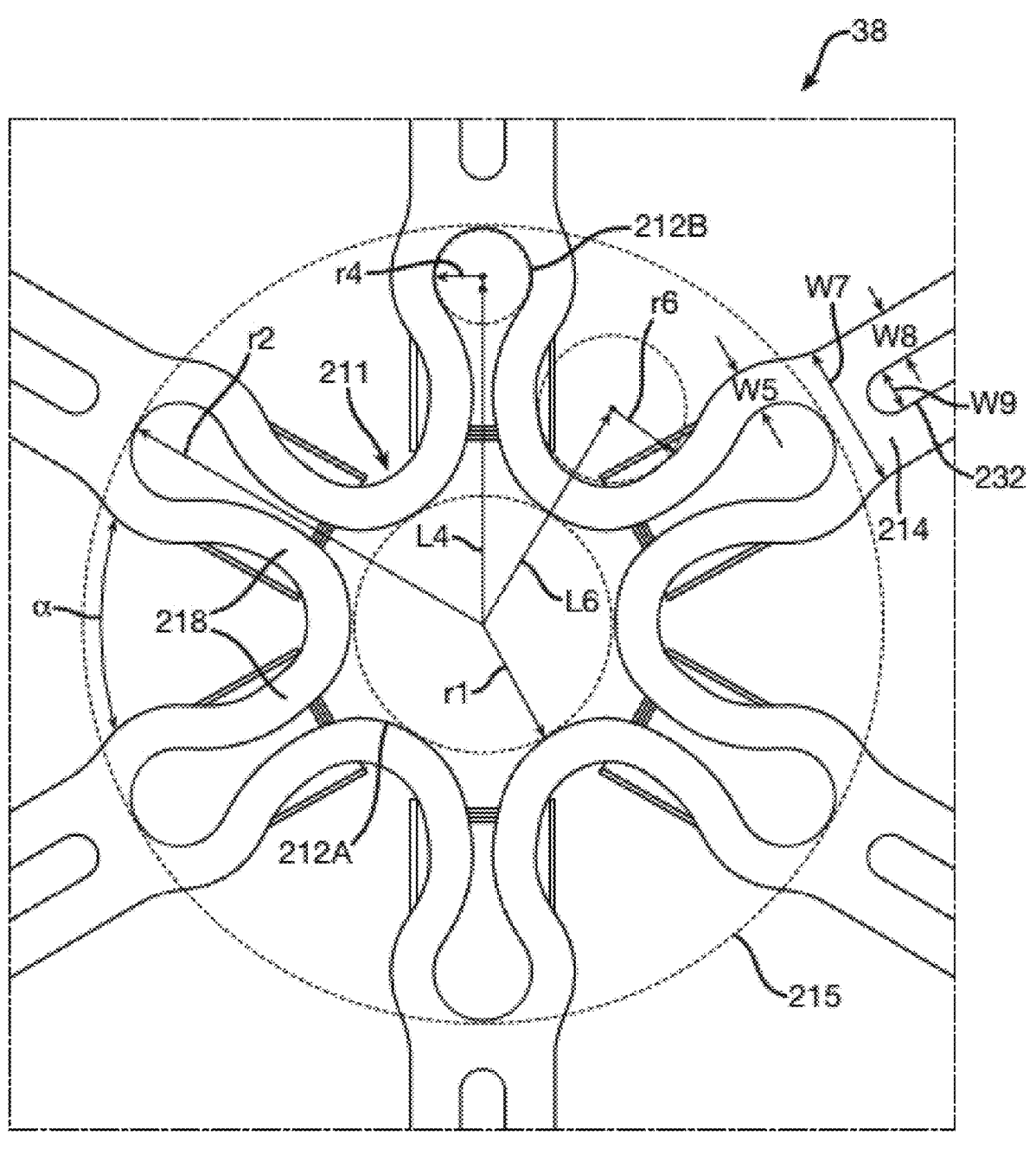

In FIG. 6I, the basket 38 may include a distal end with an aperture 212A at the approximate center (i.e., axis 86) of the spines 214 or at the central spine intersection 211. Much like FIG. 6G, the angle α between spines 214 may be approximately 60 degrees, the aperture 212A may include a radius r1 of approximately 0.2 mm to approximately 1.25 mm (e.g., approximately 0.745 mm), and the basket 38 may include a plurality of radial cutouts 212B that extend from and are connected to the aperture 212A to form a single cutout, which may result from cutting the basket 38 from tubular stock rather than planer material. The radial cutouts 212B may include a circular shape having a radius r4 of approximately 0.05 mm to approximately 0.6 mm (e.g., approximately 0.275 mm). The center of radius r4 is located at a distance L4 of approximately 1 mm to approximately 3 mm from the longitudinal axis L-L and preferably approximately 2 mm. The radial cutouts 212B may form connecting portions 218 in each spine 214 where each connecting portion 218 may have width W5 of approximately 0.12 mm to approximately 0.4 mm (e.g., approximately 0.24 mm) and where the two adjacent connecting portions 218 are connected to form a circular shape between spines 214 that has a radius r6 of approximately 0.3 mm to approximately 1.7 mm (e.g., approximately 0.78 mm). The center of radius r6 is located at a distance L6 of approximately 0.5 mm to approximately 3 mm from the central longitudinal axis L-L and preferably approximately 1.4 mm. The radial cutouts 212B may be contiguous to the inside circumference of virtual circle 215 with radius r2. In this configuration, radius r2 may be approximately 2.7 times the radius r1 of the aperture 212A. Each spine 214 may include the connecting portions 218 and a split portion extending away from the connecting portions 218 and the distal end of the basket 38. The split portion may include a slot 232 outside of the circumference of the virtual circle 215 that splits the spine 214 into two minor portions, each minor portion having a width W8 of approximately 0.1 mm to approximately 0.6 mm (e.g., approximately 0.28 mm). The width W7 of the split portion of the spine 214 may be approximately 0.4 mm to approximately 1.2 mm (e.g., approximately 0.81 mm) and the width W9 of the slot itself is approximately 0.05 mm to approximately 0.55 mm (e.g., approximately 0.25 mm).

Figure 6J:
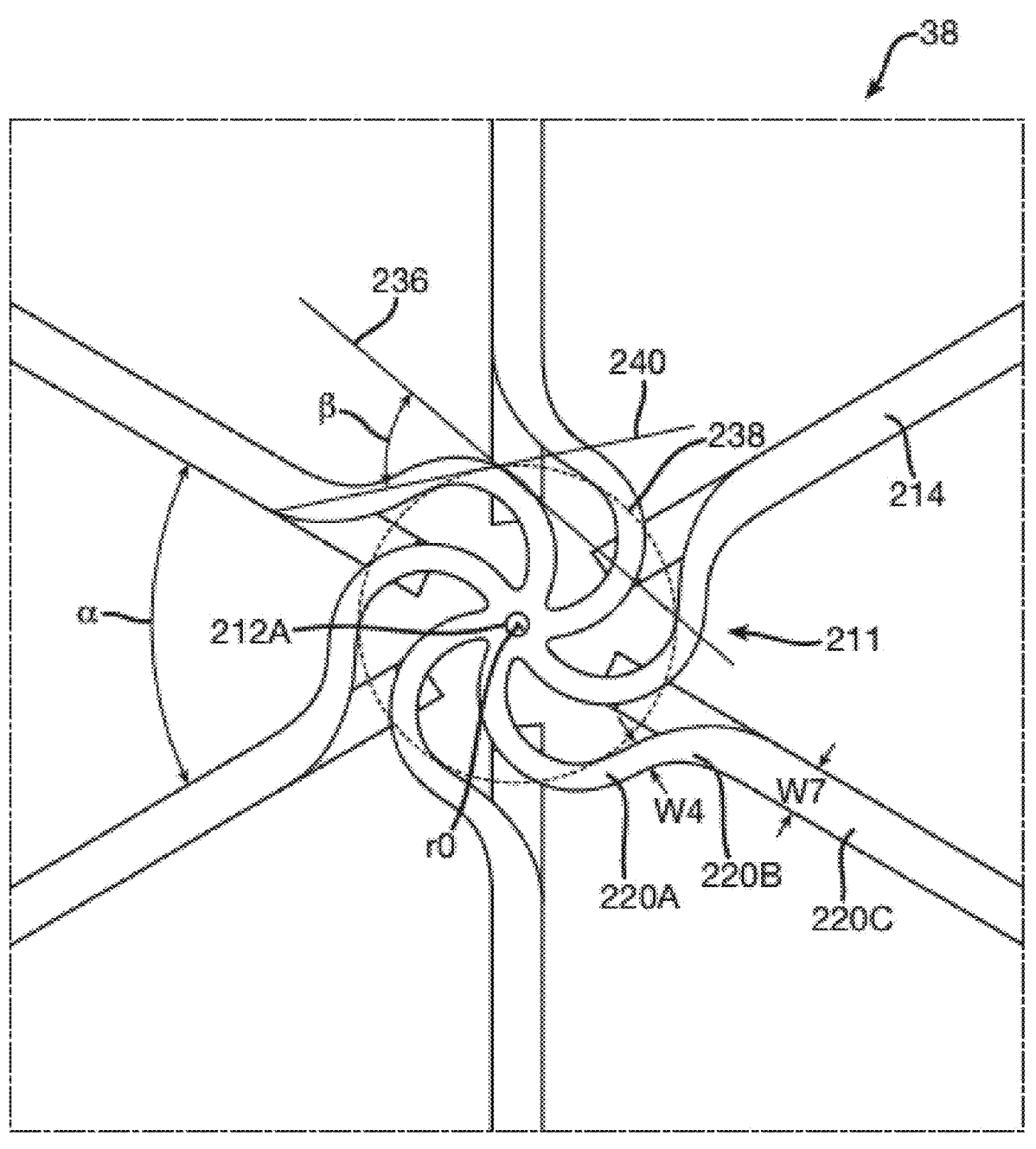

In FIG. 6J, the basket 38 may include a distal end with spines 214 forming a spiral pattern at the central spine intersection 211 and an aperture 212A at the approximate center (i.e., axis 86) of the spines 214 or the central spine intersection 211. Each spine 214 may also include a first portion 220A as a spiral with a width W4 of approximately 0.01 mm to approximately 0.5 mm (e.g., approximately 0.26 mm), a second portion 22B with a width that gradually increase from width W4 to a width W7 of third portion 220C. The width W7 of the third portion 220C of the spine 214 may be approximately 0.01 mm to approximately 1.1 mm (e.g., approximately 0.56 mm). The first portion 220A of the spines 214 may be spiral arcs that with pitch angles β of approximately 60 degrees to approximately 120 degrees (e.g., approximately 90 degrees). The pitch angle is the angle formed between a tangent of a spiral arc 236 of a first portion 220A of a spine 214 and a tangent of a virtual circle 238 centered about the spiral pattern at the point where the two lines intersect. The angle α between spines 214 may be approximately 60 degrees and the center aperture 212A may include a radius r0 of approximately 0.01 mm to approximately 0.3 mm (e.g., approximately 0.125 mm).

Figure 6K:
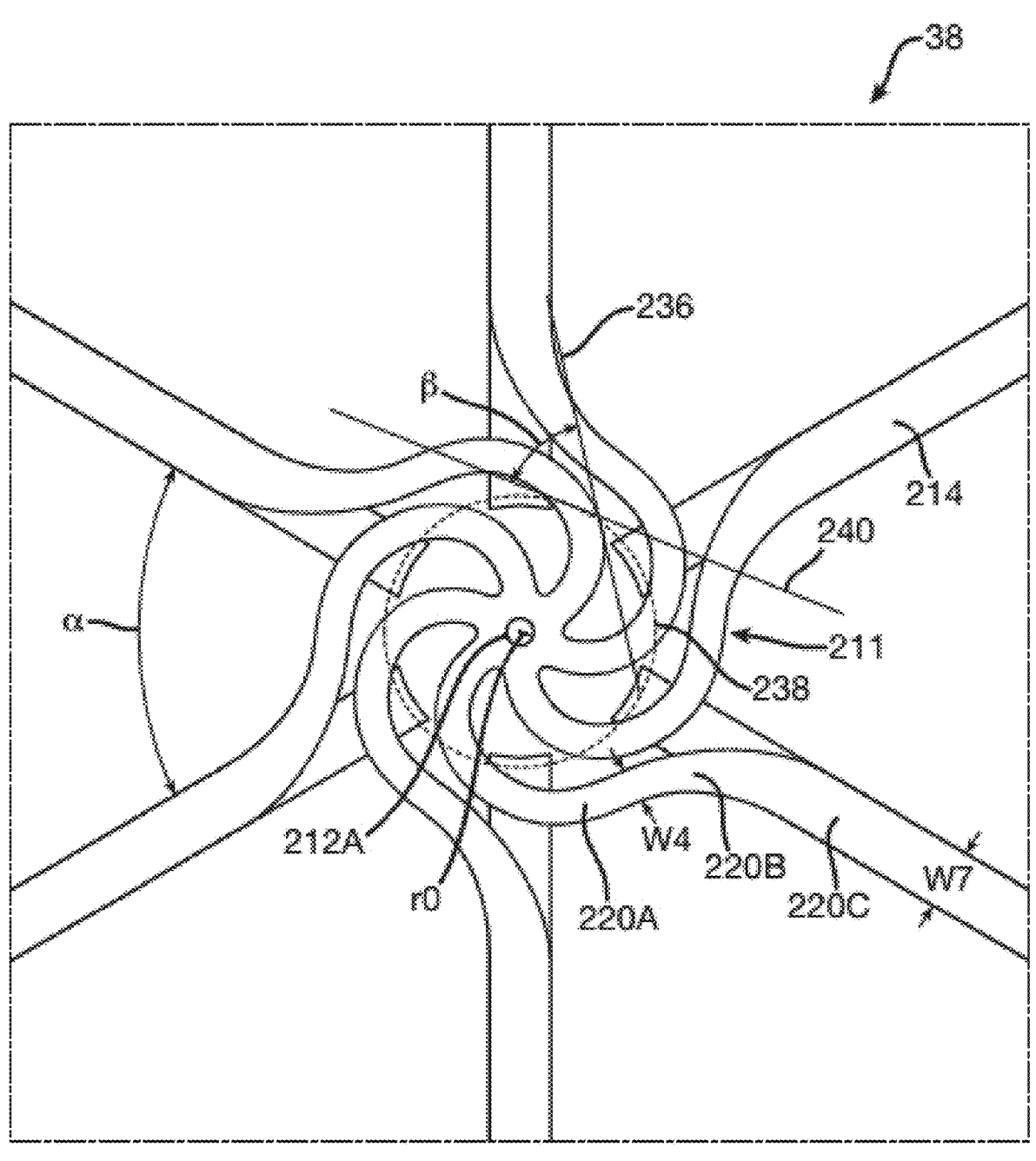

FIG. 6K illustrates a similar design as shown in FIG. 6J except that the pitch angle β is larger at approximately 90 degrees to approximately 150 degrees (e.g., approximately 120 degrees).

The spines 214 can be folded or otherwise bent such that each respective attachment end 216 of the spine 214 can be inserted into the distal end 85 of the tubular shaft 84 (as shown in FIG. 2B) and relief lands 96 of spine retention hub 90 (not shown). Although not shown in FIGS. 5A and 5B, it will be appreciated that electrodes 40 can be attached to spines 214 before the spines are inserted into the tubular shaft 84 to form the basket assembly 38. As stated previously, the spines 214 can include a flexible, resilient material (e.g., a shape-memory alloy such as nickel-titanium, also known as Nitinol) that can enable the basket assembly 38 to transition to its expanded form (as shown in FIG. 2A) when the basket assembly 38 is deployed from tubular shaft 84. As will become apparent throughout this disclosure, spines 214 can be electrically isolated from electrode 40 to prevent arcing from electrode 40 to the respective spine 214.

As will be appreciated by one skilled in the art with the benefit of this disclosure, basket assembly 38 shown in FIGS. 2A through 2C including spines 214 formed from a single sheet of planar material and converging at a central intersection is offered merely for illustrative purposes and the disclosed technology can be applicable to other configurations of basket assemblies 38. For example, the described configuration of the basket spine assemblies can be obtained via laser cutting a nitinol tube and heat treating the spines from the tubular stock into substantially the planar form shown herein. As well, the disclosed technology can be applicable to basket assemblies 38 formed from a single spine 214 or multiple spines 214 with each spine 214 being attached at both ends. In other examples, the basket assembly 38 can include a central hub connecting the multiple spines 214 together at a distal end 39 of the basket assembly 38. In yet other examples, the basket assembly 38 can include a single spine 214 configured to form a spiral, multiple spines 214 configured to form a spiral, multiple spines 214 configured to form a tripod or multiple tripods, or any other shape of basket assembly 38. Thus, although FIGS. 2A through 2C illustrate a specific configuration of basket assembly 38, the disclosed technology should not be construed as so limited.

In the exemplary embodiments shown herein, the spines width W may have a nominal width of approximately 0.6 mm and can be as low as 0.2 mm or as large as 1.5 mm. The thickness of each spine can be nominally 0.09 mm and can vary from 0.05 mm to 0.2 mm. It should be noted that these values for width and thickness can vary depending on the stiffness desired.

Referring back to FIG. 2A through FIG. 2C, one or more electrodes 40 can be attached to spines 214 to form the basket assembly 38. In some examples, each electrode 40 can include electrically conductive material (e.g., gold, platinum and palladium (and their respective alloys)).

Turning to FIGS. 7A through 7J, electrode 40 can have a variety of cross-sectional shapes, curvatures, lengths, lumen number and lumen shape as provided as examples in electrodes 740A-740E. The electrodes 740A-740E are offered to illustrate various configurations of electrodes 40 that can be used with the medical device 22 but should not be construed as limiting. One skilled in the art will appreciate that various other configurations of electrodes 40 can be used with the disclosed technology without departing from the scope of this disclosure.

Each electrode 740A-740E can have an outer surface 774 facing outwardly from electrode 740 and an inner surface 776 facing inwardly toward electrode 740 where at least one lumen 770 is formed through electrode 740. The lumen 770 can be sized and configured to receive a spine 214 such that spine 214 can pass through electrode 740. Lumen 770 can be a symmetric opening through electrode 740A-740E and can be disposed offset with respect to a longitudinal axis L-L of the respective electrode. In other examples, lumen 770 can pass through electrode 740 in a generally transverse direction with respect to the longitudinal axis L-L of the respective electrode. Furthermore, lumen 770 can be positioned in electrode 740 nearer a bottom surface, nearer a top surface, or nearer a middle of electrode 740 depending on the particular configuration. In FIGS. 7A, 7C, and 7E through 7J, the top surface (upper side) is oriented toward the top of the drawing, the bottom surface (lower side) is oriented toward the bottom of the drawing, and the middle is between the top surface and the bottom surface. In other words, each electrode 740A-740E can include a lumen 770 that is offset with respect to a centroid of the electrode 740A-740E.

In addition, as shown in FIGS. 7A through 7F, electrodes 740A-740C can have a wire relief 772 forming a recess or depression in electrode 740 adjacent lumen 770 for one or more wires to pass through lumen 770 along with a respective spine 214. Relief 772 can be sized to provide room for a wire of electrode 740 to pass through electrode 740 such that electrode 740 can be in electrical communication with the control console 24.

Alternatively, or in addition thereto, wires can pass through a wire lumen 773 as shown in example electrodes 740D and 740E in FIGS. 7G through 7J. Although not depicted, electrodes 40 may include both a wire relief 772 adjacent lumen 770 and wire lumen 773. Such electrode may permit additional wires to pass through the electrode body.

Figure 7A:
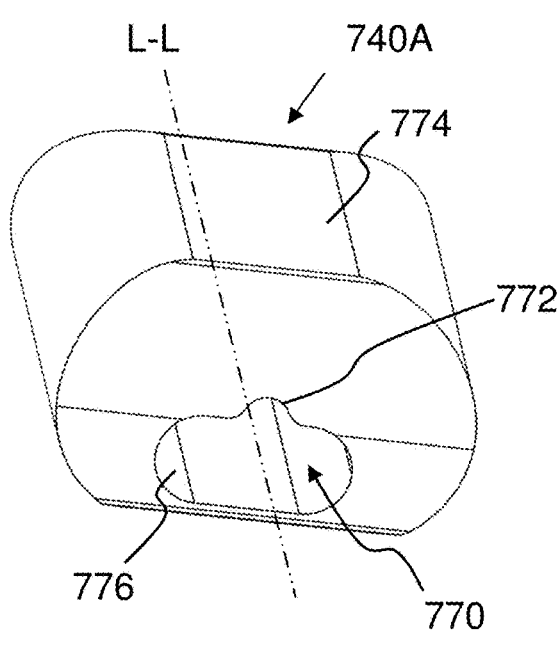
FIGS. 7A, 7B, 7C, 7D, 7E, 7F, 7G, 7H, 7I, and 7J are schematic pictorial illustrations showing a perspective view of various example electrodes, in accordance with embodiments of the present invention.
Figure 7B:
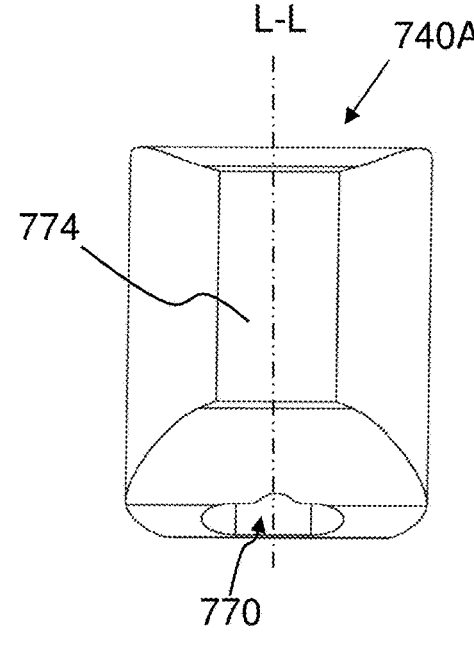
Figure 7C:
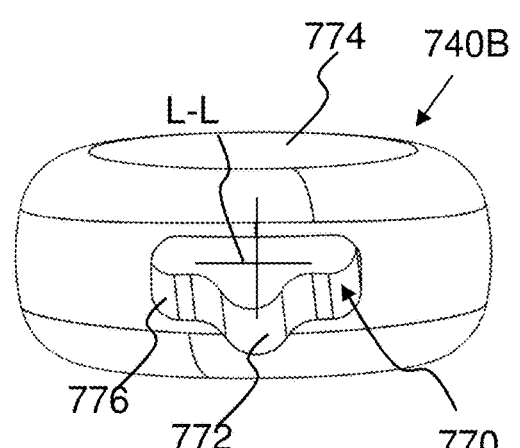
Figure 7D:
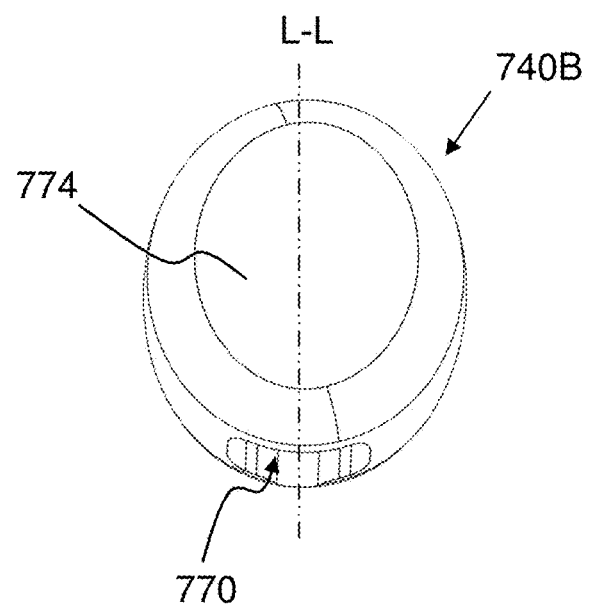
Figures 7E, 7F, 7G, 7H, 7I, 7J:
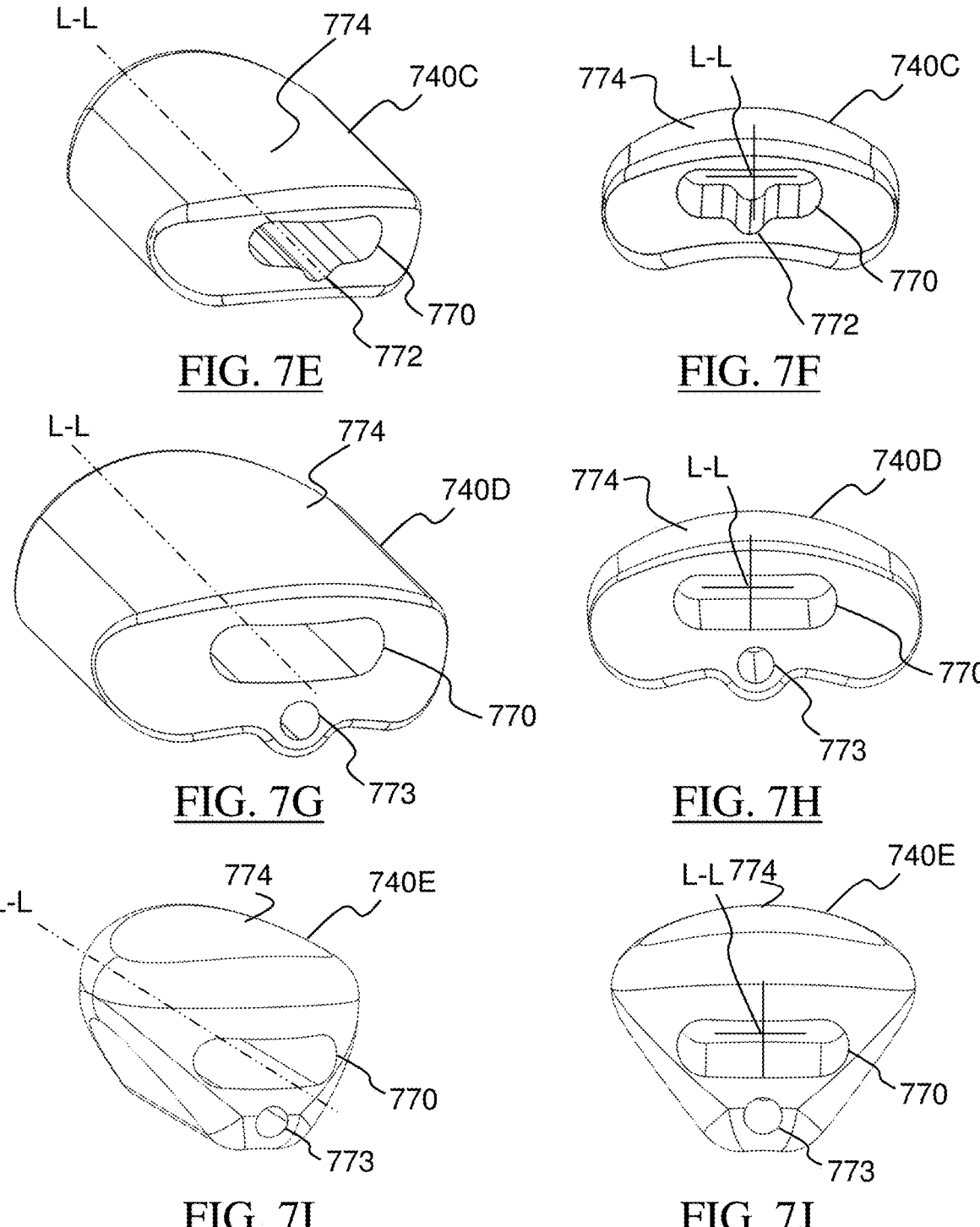

As shown in FIGS. 7A-7J, the electrodes 740A-740E can include various shapes depending on the application. For example, as illustrated in FIGS. 7A and 7B, the electrode 740A can have a substantially rectangular cuboid shape with rounded edges. In other examples, the electrode 740B can have a substantially ovoid shape (as illustrated in FIGS. 7C and 7D), the electrode 740C, 740D can have a contoured shape including a convex side and a concave side (as illustrated in FIGS. 7E through 7H), or the electrode 740E can have a contoured shape including substantially more material proximate an upper side than a lower side of the electrode 740E (as illustrated in FIGS. 71 and 7J). As will be appreciated by one of skill in the art, the various example electrodes 740A-740E shown in FIGS. 7A-7J, and described herein, are offered for illustrative purposes and should not be construed as limiting.

Figure 8A:
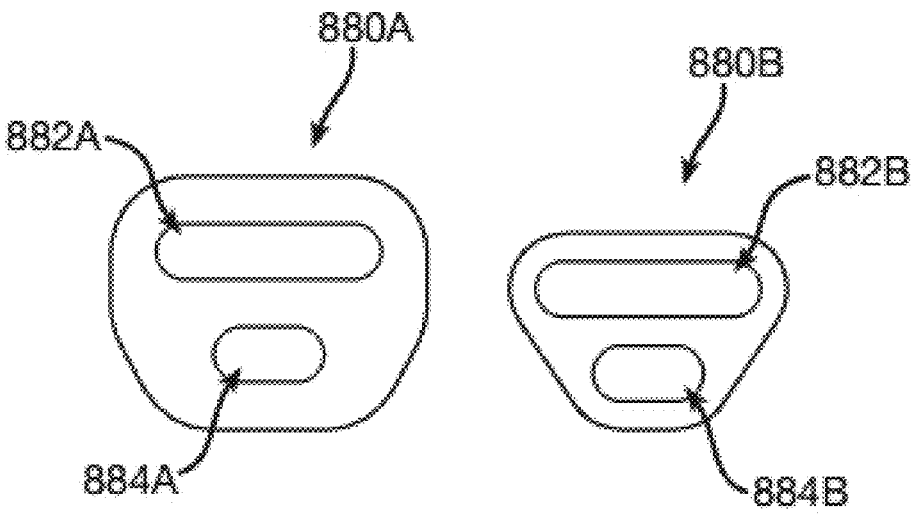
FIGS. 8A and 8B are schematic pictorial illustrations showing various insulative jackets of a given medical device, in accordance with embodiments of the present invention.
Figure 8B:
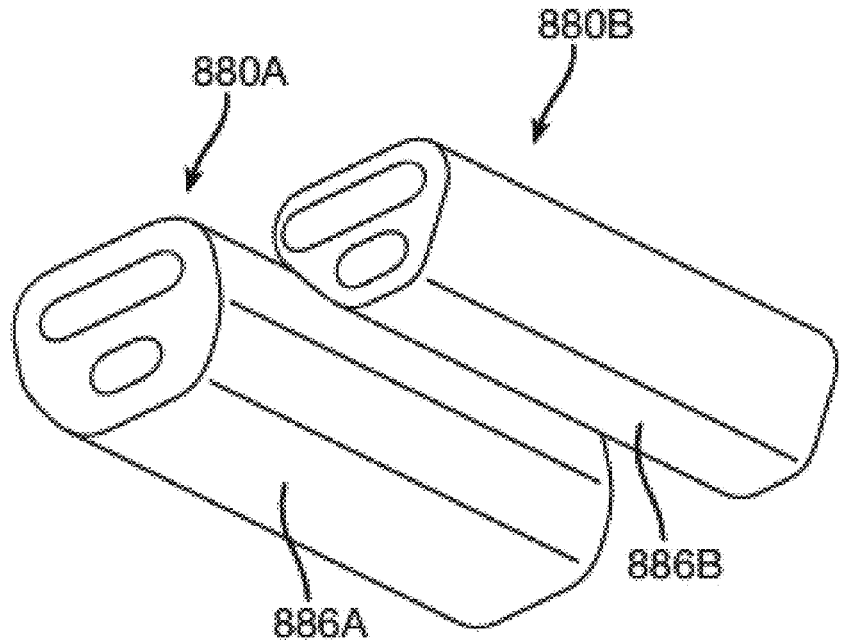

FIGS. 8A and 8B are schematic pictorial illustrations showing various insulative jackets 880A, 880B of a given medical device 22, in accordance with embodiments of the present invention. FIG. 8A is a front view while FIG. 8B is a perspective view of insulative jackets 880A, 880B. Insulative jackets 880A, 880B can be made from a biocompatible, electrically insulative material such as polyamide-polyether (Pebax) copolymers, polyethylene terephthalate (PET), urethanes, polyimide, parylene, silicone. In some examples, insulative material can include biocompatible polymers including, without limitation, polyetheretherketone (PEEK), polyglycolic acid (PGA), poly (lactic-co-glycolic acid) copolymer (PLGA), polycaprolactive (PCL), poly(3-hydroxybutyrate-co-3-hydroxyvalerate) (PHBV), poly-L-lactide, polydioxanone, polycarbonates, and polyanhydrides with the ratio of certain polymers being selected to control the degree of inflammatory response. Insulative jackets 880A, 880B may also include one or more additives or fillers, such as, for example, polytetrafluoroethylene (PTFE), boron nitride, silicon nitride, silicon carbide, aluminum oxide, aluminum nitride, zinc oxide, and the like. Insulative jacket 880A, 880B can help to insulate a spine 214 and/or wires passing through insulative jacket 880A, 880B from electrode 40 to prevent arcing from electrode 40 to the spine 214 and/or mechanical abrasion of wires passing through insulative jacket 880A, 880B.

As illustrated in FIGS. 8A and 8B, insulative jackets 880A, 880B, can include a cross-sectional shape that is substantially trapezoidal. The insulative jacket may consist of a single lumen or multi-lumen configuration. Multi-lumen jackets may be configured such that the alloy frame and wires share a single lumen while the second lumen may be used for irrigation. The alloy frame and wires may occupy separate lumens, also, as described. The current embodiment does not utilize irrigated jackets. For these designs, the insulative jackets may be continuous (individual sleeves extending from proximal to distal end of each alloy frame strut), segmented (bridging between electrode gaps), or a combination of both. Furthermore, insulative jacket 880A, 880B can include a first lumen 882A, 882B and a second lumen 884A, 884B. First lumen 882A, 882B can be configured to receive spine 214 while second lumen 884A, 884B can be configured to receive a wire, or vice-versa. In other examples, first lumen 882A, 882B and second lumen 884A, 884B can each be configured to receive one or more wires that can be connected to one or more electrodes 40. Furthermore, as illustrated in FIG. 8B, insulative jacket 880A, 880B can include an aperture 886A, 886B through which a wire can be electrically connected to electrode 40. Although illustrated in FIG. 8B as being proximate a bottom of insulative jacket 880A, 880B, aperture 886A, 886B can be positioned proximate a top or side of insulative jacket 880A, 880B. Furthermore, insulative jacket 880A, 880B can include multiple apertures 886A, 886B with each aperture being disposed on the same side of insulative jacket (i.e., top, bottom, left, right) or on different sides of the insulative jacket depending on the application.

Figure 9:
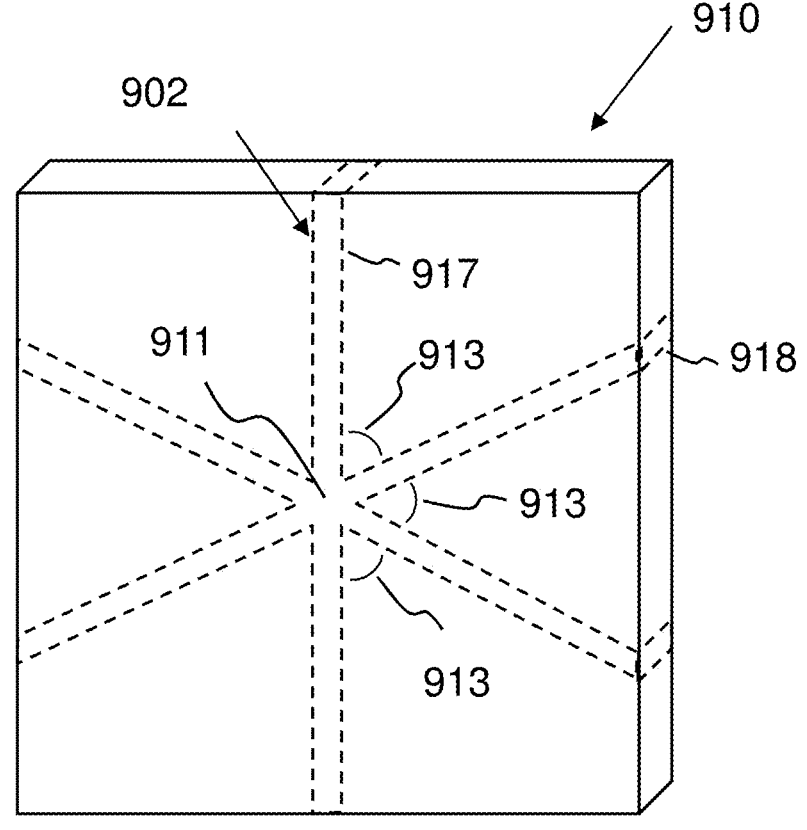
FIG. 9 is a schematic pictorial illustration of a method of cutting a plurality of linear spines from a planar sheet of material, in accordance with an embodiment of the present invention.
Figures 10A, 10B:
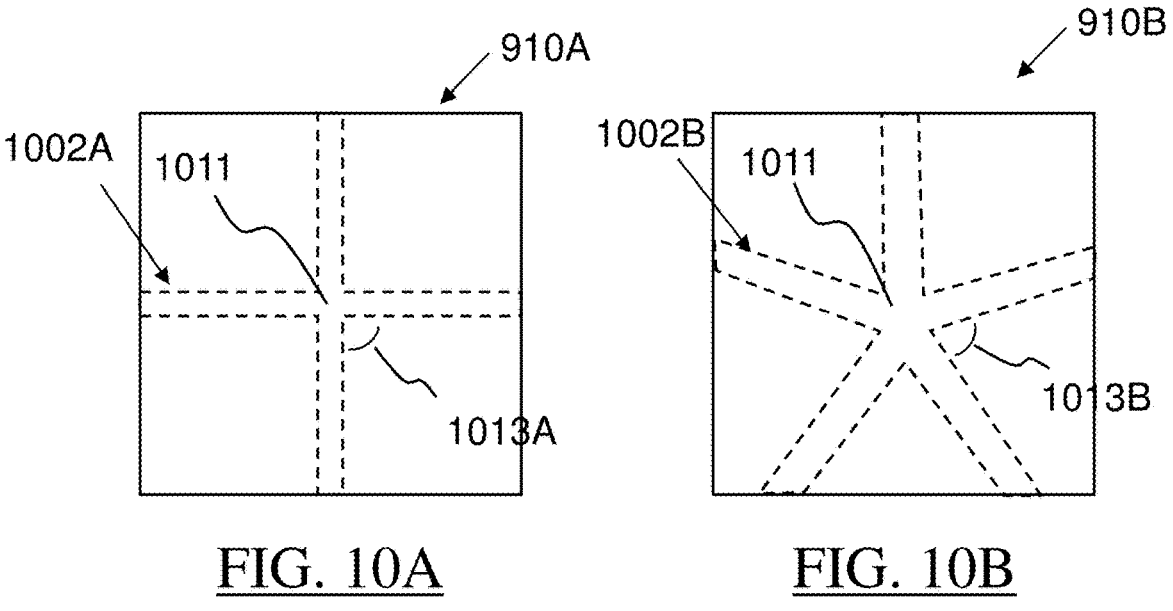
FIGS. 10A, 10B, 10C, and 10D are schematic pictorial illustrations of a method of cutting a plurality of linear spines from a planar sheet of material, in accordance with an embodiment of the present invention.
Figures 10C, 10D:
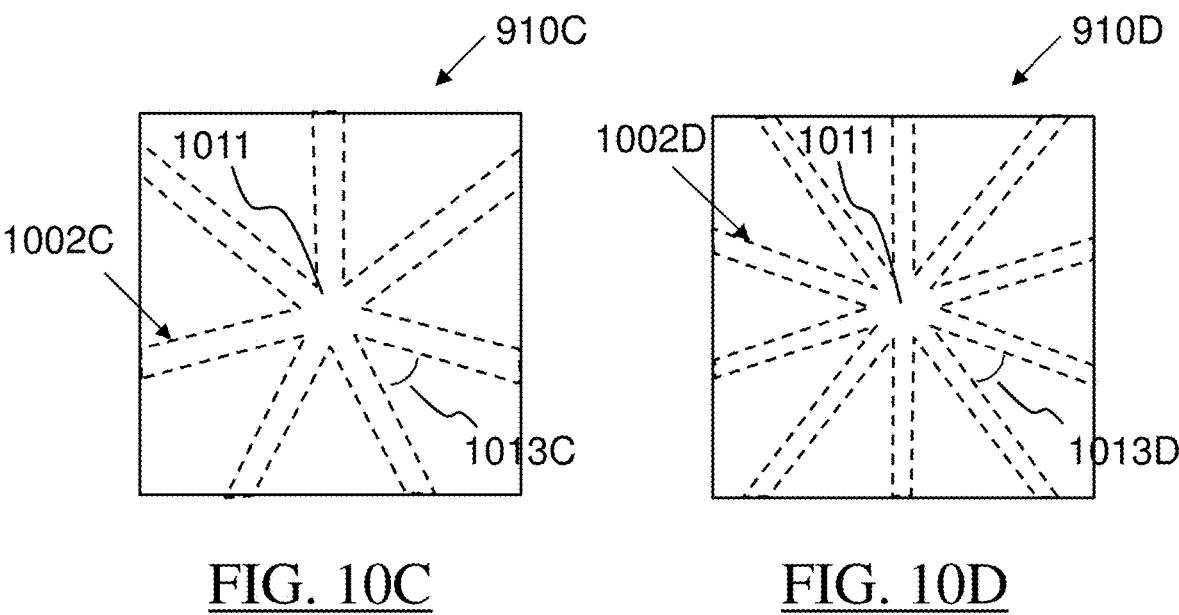

FIGS. 9 and 10A-10D are schematic pictorial illustrations of cutting patterns for various linear spines patterns 902 from a planar sheet of material 910. As described supra, planar sheet of material 910 can include a number of spines 214 ranging from about four to about ten spines. As illustrated in FIG. 9, planar sheet of material 910 can include central intersection 911 and spine pattern 902, which includes one or both of longitudinal scores 917 and transverse scores 918. In any of the embodiments disclosed herein, planar sheet of material 910 can also include a central intersection 911 and spine patterns 902 including an equiangular pattern 913. Planar sheet of material 910 can include spine patterns including a number of spine patterns 902 forming spines 214 in basket assembly 38. As would be understood by one of skill in the art, adjusting the number of spine patterns 902 may impact a number of factors including, without limitation, stability, flexibility, surface contact, and ablation capacity of medical probe 22.

FIGS. 10A through 10D provide example spine patterns 1002A, 1002B, 1002C, 1002D, although additional spine patterns are contemplated. Similar to the above planar sheet of material 910, spine patterns 1002A-1002D can include a respective central intersection 1011 and a respective equiangular pattern 1013A-1013D. As would be appreciated by one of skill in the art, as the number of spines added to spine pattern 1002A-1102D, the angle for equiangular pattern 1013A-1013D may change. In each of these examples provided, planar sheet of material 910A, 910B, 910C, 910D may also include central intersections and spine patterns including equiangular patterns. Although not depicted in FIGS. 10A-10D, planar sheet of material 910A-910D can include one or both of longitudinal scores 917 and transverse scores 918.

Figure 11A:
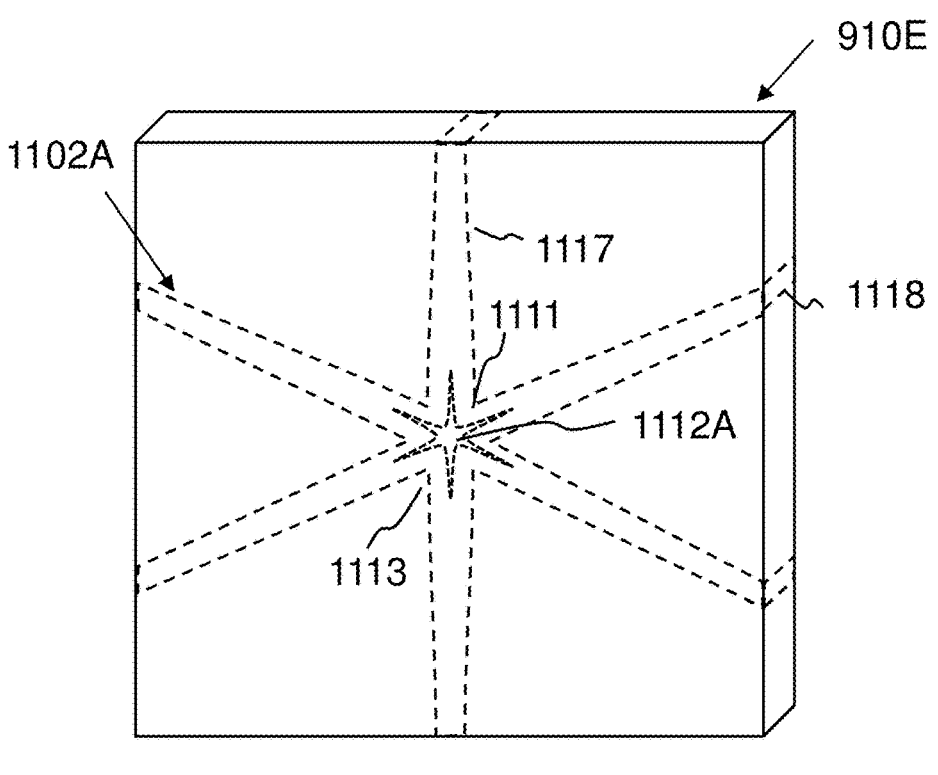
FIGS. 11A and 11B are schematic pictorial illustrations of a method of cutting a plurality of linear spines including one or more cutouts at a central spine intersection from a planar sheet of material, in accordance with an embodiment of the present invention.
Figure 11B:
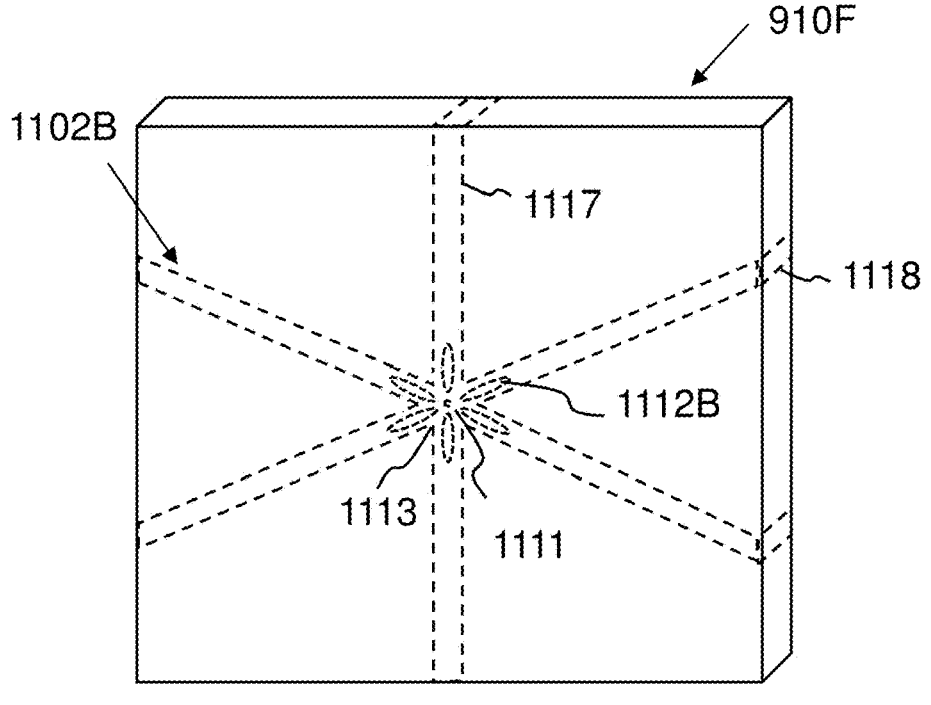

FIGS. 11A and 11B are schematic pictorial illustrations of cutting patterns for various linear spine patterns including one or more cutouts at a central spine intersection from a planar sheet of material. As described supra, planar sheet of material 910E, 910F may include a spine pattern 1102A including one cutout 1112A at central intersection 1111 or a spine pattern 1102B including two or more cutouts 1112B at central intersection 1111. As illustrated in FIGS. 11A and 11B, planar sheet of material 910E and 910F can include one or both of longitudinal scores 1117 and transverse scores 1118.

FIG. 12 is a flowchart illustrating a method 1200 of manufacturing a basket assembly 38, in accordance with an embodiment of the present invention. Method 1300 can include cutting 1202 a planar sheet of material 910 or a tubular material to form a plurality of linear spines 214 including a central spine intersection 211. Cutting 1202 the plurality of linear spines 214 can include cutting from a pattern 9002 (or 1002A-1002D) including longitudinal and transverse scores 917, 918. The planar sheet of resilient material can include shape-memory alloy such as nickel-titanium (also known as Nitinol), cobalt chromium, or any other suitable material. Method 1200 can include cutting 1204 one or more discrete cutouts 212 at the central spine intersection 211. As described supra, the one or more discrete cutouts 212 can be a single cutout or two or more cutouts. In addition, the one or more discrete cutouts 212 can be cut in a pattern to extend along at least a portion of each spine. In some examples, steps 1202 and 1204 may occur as simultaneous steps or as a sequence of steps. As an alternative to steps 1202 and 1204, metallic strands can be shaped similar to the pattern formed by cutting the planar sheet in steps 1202 and 1204.

Method 1200 can optionally include inserting 1206 each spine into a lumen of at least one electrode. The electrodes can be positioned such that the electrodes are offset between electrodes on adjacent spines. Method 1200 can optionally include fitting 1308 ends of the plurality of linear spines to a tubular shaft sized to traverse vasculature such that the central spine intersection is positioned at a distal end of the medical probe and respective spines are movable from a tubular configuration to a bowed configuration. As will be appreciated by one of skill in the art including the benefit of this disclosure, fitting 1208 an end of the spine into a tubular shaft can include attaching the spine 214 to a spine retention hub 90. Furthermore, the spine retention hub 90 and/or the spine 214 and the tubular shaft 84 can be inserted into a flexible insertion tube 30 to form the medical probe 22.

In some examples, the method can also include forming an approximately spheroid or oblate-spheroid shape with the linear spines. Method 1200 can further include electrically connecting the wire to the one or more electrodes. Method 1200 can also include disposing an insulative sleeve over the linear spines and within the lumen of the respective electrode.

As will be appreciated by one skilled in the art, method 1200 can include any of the various features of the disclosed technology described herein and can be varied depending on the particular configuration. Thus, method 1200 should not be construed as limited to the particular steps and order of steps explicitly described herein. It is noted that while the preference for the exemplary embodiments of the medical probe is for IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

The embodiments described above are examples, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

What is claimed is:

1. An expandable basket assembly for a medical probe, comprising:
a single unitary structure comprising a plurality of spines converging at a central spine intersection, the central spine intersection being positioned on a longitudinal axis of the expandable basket assembly at a distal end thereof; and
a plurality of radial cutouts with each radial cutout defining an opening in each of the plurality of spines proximate the central spine intersection so that each opening extends for a length along each spine away from the central spine intersection,
each cutout comprises a tadpole shaped cutout, the tadpole shaped cutout includes a head portion contiguous to a circumference of a first virtual circle with a first radius r1 disposed about the longitudinal axis, the head portion defining a negative area approximating a second virtual circle with a second radius r2, the head portion connected to a slotted tail portion extending for a first length L1 along the spine and contiguous to an inside circumference of a third virtual circle having a third radius r3, and
the first length of the slotted tail portion is approximately 6-10 times that of the length of the first radius r1 of the first virtual circle.

2. The expandable basket assembly according to claim 1, further comprising a center aperture disposed on the central spine intersection, wherein the plurality of radial cutouts are separated from the center aperture by a portion of the central spine intersection.

3. The expandable basket assembly of claim 1, further comprising a center cutout disposed on the longitudinal axis to define a central negative area of a center aperture approximating a central circle including a central radius r0 smaller than the first radius r1.

4. The expandable basket assembly of claim 3, in which the negative area of each of the tadpole shaped cutouts comprises approximately 0.2 mm-squared while the negative area of the center aperture is approximately 0.05 mm-squared so that a total negative area defined by all of the cut outs is approximately 1.4 mm-squared.

5. The expandable basket assembly of claim 3, wherein central void radius r0 comprises approximately 0.13 mm, the second radius r2 comprises approximately 0.2 mm, and the first radius r1 comprises approximately 0.23 mm.

6. An expandable basket assembly for a medical probe, comprising:
a single unitary structure comprising a plurality of spines converging at a central spine intersection, the central spine intersection being positioned on a longitudinal axis of the expandable basket assembly at a distal end thereof;
a plurality of radial cutouts with each radial cutout defining an opening in each of the plurality of spines proximate the central spine intersection so that each opening extends for a length along each spine away from the central spine intersection, and a center aperture disposed on the central spine intersection, wherein the plurality of radial cutouts are separated from the center aperture by a portion of the central spine intersection, the center aperture comprises an area of about 0.01 mm-squared to about 0.4 mm-squared, each of the plurality of radial cutouts includes an area of about 0.1 mm-squared to about 0.55 mm-squared and each of the spines includes a first portion proximate to the central spine intersection with a first width, a second portion proximate the first portion with a second width less than the first portion, and a third portion proximate the second portion with a third width that is greater than the first width and greater than the second width, each of the plurality of radial cutouts defines a comet-shaped cutout with head portion with a slotted tapered tail extending to a proximal portion of each spine.

7. The expandable basket assembly according to claim 6, wherein the first width is about 0.15 mm to about 0.5 mm, the second width is about 0.05 mm to about 0.35 mm, and the third width is about 0.3 mm to about 0.7 mm, and the third portion of each spine comprises an electrode attachment slot configured to accept an electrode, the electrode attachment slot bisects each spine into two minor widths of about 0.05 mm to about 6 mm.

8. An expandable basket assembly for a medical probe, comprising:

a single unitary structure comprising a plurality of spines converging at a central spine intersection, the central spine intersection being positioned on a longitudinal axis of the expandable basket assembly at a distal end thereof; and a plurality of radial cutouts with each radial cutout defining an opening in each of the plurality of spines proximate the central spine intersection so that each opening extends for a length along each spine away from the central spine intersection, a center aperture disposed on the central spine intersection, wherein the plurality of radial cutouts are separated from the center aperture by a portion of the central spine intersection, wherein each cut out comprises two teardrop cutouts attached at their narrow portions to define a single cutout on each spine of about 0.4 mm-squared.

9. The expandable basket assembly according to claim 6, wherein the third portion of each spine comprises a slot that bisects each spine into two minor widths each of which comprises a width of approximately 0.1 mm to approximately 6 mm.

10. The expandable basket assembly according to claim 6, wherein the third portion of each spine comprises a slot that bisects each spine into two minor portions with the slot comprising a width of approximately 0.05 mm to approximately 0.55 mm and the center aperture includes a radius of approximately 0.4 mm to approximately 1.2 mm.

11. The expandable basket assembly according to claim 8, wherein each radial cutout comprises an ellipse shape at an end furthest from the center aperture and the ellipse shape includes a length of about 0.20 mm to about 0.55 mm and a width of about 0.1 mm to about 0.45 mm.

12. The expandable basket assembly according to claim 1, further comprising a center aperture disposed on the central spine intersection, wherein the plurality of radial cutouts extend from and are connected to the center aperture to form a single cutout.

13. The expandable basket assembly according to claim 1, each of the spines includes a first portion proximate to the central spine intersection with a first width, a second portion proximate the first portion with a second width less than the first portion, and a third portion proximate the second portion with a third width that is greater than the first width and greater than the second width, wherein the first width is about 0.15 mm to about 0.5 mm, the second width is about 0.05 mm to about 0.35 mm, and the third width is about 0.3 mm to about 0.7 mm.

14. The expandable basket assembly according to claim 1, each of the spines includes a first portion proximate to the central spine intersection with a first width, a second portion proximate the first portion with a second width less than the first portion, and a third portion proximate the second portion with a third width that is greater than the first width and greater than the second width, wherein the third portion of each spine comprises an electrode attachment slot configured to accept an electrode, the electrode attachment slot bisects each spine into two minor widths of about 0.05 mm to about 6 mm.

15. The expandable basket assembly according to claim 1, each of the spines includes a first portion proximate to the central spine intersection with a first width, a second portion proximate the first portion with a second width less than the first portion, and a third portion proximate the second portion with a third width that is greater than the first width and greater than the second width, wherein the third portion of each spine comprises a slot that bisects each spine into two minor widths each of which comprises a width of approximately 0.1 mm to approximately 6 mm.

16. The expandable basket assembly according to claim 8, each of the spines includes a first portion proximate to the central spine intersection with a first width, a second portion proximate the first portion with a second width less than the first portion, and a third portion proximate the second portion with a third width that is greater than the first width and greater than the second width, wherein the first width is about 0.15 mm to about 0.5 mm, the second width is about 0.05 mm to about 0.35 mm, and the third width is about 0.3 mm to about 0.7 mm.

17. The expandable basket assembly according to claim 8, each of the spines includes a first portion proximate to the central spine intersection with a first width, a second portion proximate the first portion with a second width less than the first portion, and a third portion proximate the second portion with a third width that is greater than the first width and greater than the second width, wherein the third portion of each spine comprises an electrode attachment slot configured to accept an electrode, the electrode attachment slot bisects each spine into two minor widths of about 0.05 mm to about 6 mm.

18. The expandable basket assembly according to claim 8, each of the spines includes a first portion proximate to the central spine intersection with a first width, a second portion proximate the first portion with a second width less than the first portion, and a third portion proximate the second portion with a third width that is greater than the first width and greater than the second width, wherein the third portion of each spine comprises a slot that bisects each spine into two minor widths each of which comprises a width of approximately 0.1 mm to approximately 6 mm.

19. The expandable basket assembly according to claim 8, each of the spines includes a first portion proximate to the central spine intersection with a first width, a second portion proximate the first portion with a second width less than the first portion, and a third portion proximate the second portion with a third width that is greater than the first width and greater than the second width, wherein the third portion of each spine comprises a slot that bisects each spine into two minor portions with the slot comprising a width of approximately 0.05 mm to approximately 0.55 mm.

* * * * *